United States Patent
Takeda et al.

(10) Patent No.: US 7,599,054 B2
(45) Date of Patent: *Oct. 6, 2009

(54) PATTERN INSPECTION APPARATUS

(75) Inventors: Masayoshi Takeda, Hitachinaka (JP); Hirokazu Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/073,083

(22) Filed: Feb. 29, 2008

(65) Prior Publication Data

US 2008/0162065 A1 Jul. 3, 2008

Related U.S. Application Data

(63) Continuation of application No. 11/298,749, filed on Dec. 12, 2005, now Pat. No. 7,355,693.

(30) Foreign Application Priority Data

Dec. 17, 2004 (JP) ............................. 2004-366501

(51) Int. Cl.
*G01N 21/00* (2006.01)
(52) U.S. Cl. ............... 356/237.5; 356/237.1; 356/237.2
(58) Field of Classification Search .... 356/237.1–241.6
See application file for complete search history.

(56) References Cited

U.S. PATENT DOCUMENTS

| | | | | |
|---|---|---|---|---|
| 5,578,821 A | * | 11/1996 | Meisberger et al. | 250/310 |
| 7,292,327 B2 | * | 11/2007 | Nara et al. | 356/237.2 |
| 7,355,693 B2 | * | 4/2008 | Takeda et al. | 356/237.5 |
| 2002/0057831 A1 | * | 5/2002 | Hiroi et al. | 382/149 |
| 2002/0171051 A1 | * | 11/2002 | Nakagaki et al. | 250/559.4 |

FOREIGN PATENT DOCUMENTS

JP  2000-161392 A  6/2000

* cited by examiner

*Primary Examiner*—Gregory J Toatley, Jr.
*Assistant Examiner*—Jarreas C Underwood
(74) *Attorney, Agent, or Firm*—McDermott Will & Emery LLP

(57) ABSTRACT

The defect confirmation screen of a pattern inspection apparatus that allows the user to create a recipe and check defects easily and quickly includes a "map display part" where a wafer map is displayed, an "image display part" where a list of defect images is displayed, a "list display part" where detailed information on defects is displayed and set, and a "graph display part" where a graph is displayed for selected defect items. Those display parts cooperate with each other and change the defect images, defect information list, and defect graph according to selected map information. A classification code, a clustering condition, and a display filter entered using the information described above are registered in a recipe.

17 Claims, 19 Drawing Sheets

FIG. 9A

MAP DRAWING MODE

MODE FOR DISPLAYING WHOLE WAFER

MODE FOR DISPLAYING ONE OR MORE OVERLAPPED DIES OF WAFER

MODE FOR DISPLAYING ONE OR MORE OVERLAPPED WAFER SHOTS OF WAFER

FIG. 9B

MAP OPERATION

OPERATION FOR SELECTING A DEFECT IN THE MAP

OPERATION FOR SELECTING A DEFECT IN AN AREA IN THE MAP

OPERATION FOR SCALING AN AREA IN THE MAP

FIG. 14

DISPLAY CONDITION DIALOG

| VALID | FILTER ITEM | MINIMUM VALUE | MAXIMUM VALUE |
|---|---|---|---|
| ☐ | DEFECT COORDINATES | 0.0 | 99999.9 |
| ☐ | DEFECT DIE ADDRESS | 0 | 99 |
| ■ | DEFECT AREA | 0.00000 | 999.99999 |
| ☐ | DEFECT SIZE | 0.0 | 99999.9 |
| ☐ | ASPECT RATIO | 0.00 | 99.99 |
| ☐ | CLASSIFICATION CODE | 0 | 2.55 |
| ☐ | CLUSTER No. | 0 | 999999 |
| ■ | SHADING DIFFERENCE | -999 | 999 |

| VALID | FILTER ITEM | | |
|---|---|---|---|
| ☐ | RADIUS | | mm ▼ |
| ■ | INSPECTION METHOD | CELL INSPECTION ▼ | |
| ☐ | SELECT No. OF ITEMS | | ITEMS |

| CLUSTERING METHOD | IN-DIE MERGE DISTANCE ▶ |
|---|---|
| IN-DIE MERGE DISTANCE | 50.0 μm |
| MINIMUM No. OF ELEMENTS | 10 ITEMS |

NO. OF CLUSTER GROUPS 18

[EXECUTE] [CANCEL] [CLOSE]

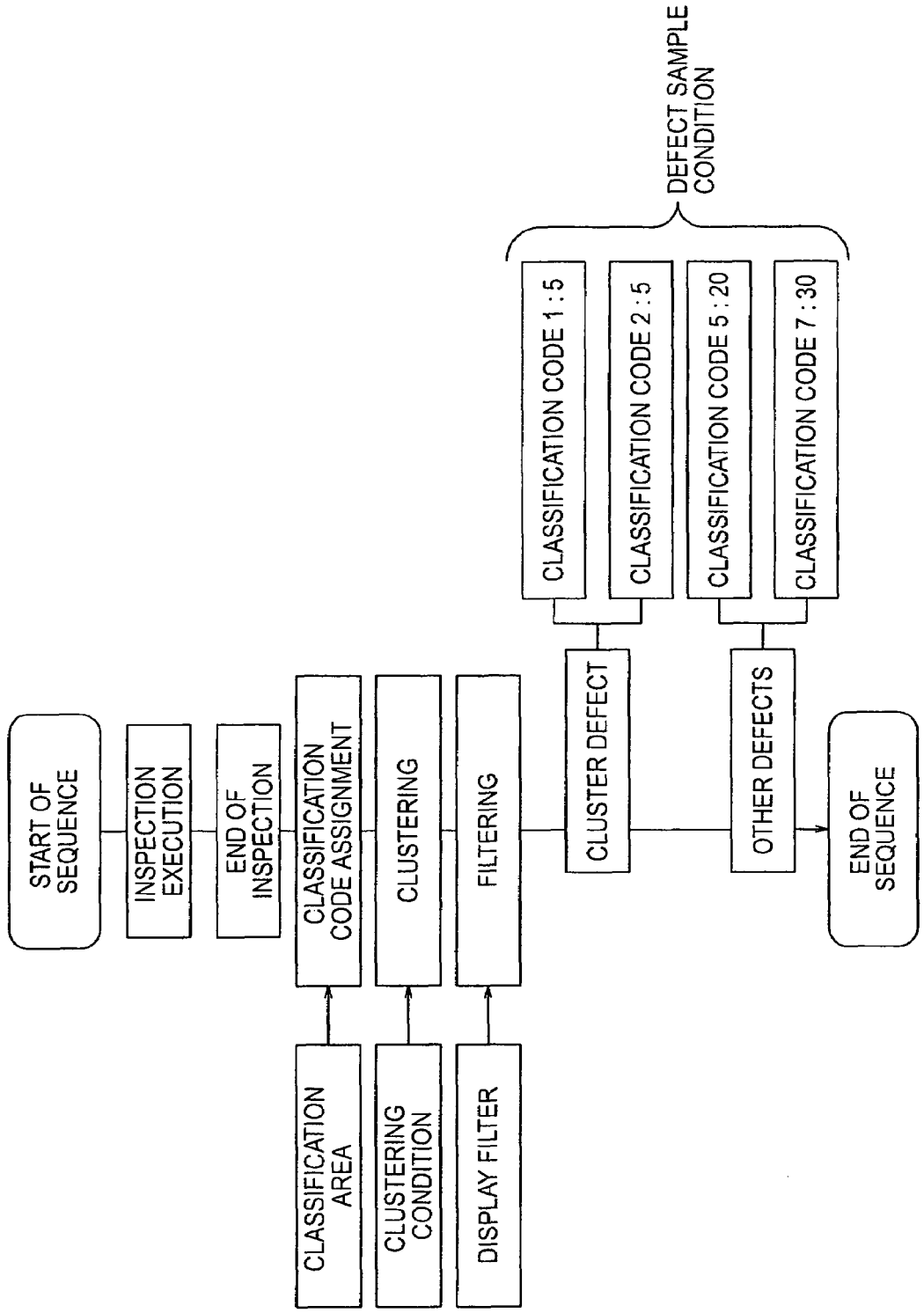

DEFECT MAP IMMEDIATELY AFTER INSPECTION

DEFECT MAP GENERATED WHEN DEFECTS ARE RANDOMLY SAMPLED

DEFECT MAP IMMEDIATELY AFTER INSPECTION

DEFECT MAP GENERATED WHEN DEFECTS ARE SAMPLED USING THE METHOD ACCORDING TO THE PRESENT INVENTION

PATTERN INSPECTION APPARATUS

This application is a Continuation of U.S. application Ser. No. 11/298,749, filed Dec. 12, 2005, now U.S. Pat. No. 7,355,693, claiming priority of Japanese Application No. 2004-366501, filed Dec. 17, 2004, the entire contents of each of which are hereby incorporated by reference.

BACKGROUND OF THE INVENTION

The present invention relates to an inspection apparatus for a substrate having micro patterns thereon such as a semiconductor wafer or a liquid crystal panel.

For example, semiconductor devices are fabricated by repeatedly transferring a pattern, formed as a photo-mask, on a semiconductor wafer through lithography processing and etching processing. Because whether or not lithography processing and etching processing are performed successfully and whether or not foreign matter is generated in the semiconductor device fabrication stage largely affect the fabrication yield of semiconductors, it is necessary to detect the generation of abnormal conditions or defects as soon as possible or in advance. To meet this need, a pattern on a semiconductor wafer is inspected during the fabrication stage using a beam or an electron beam. (JP-A-2000-161932).

Conventionally, the screen function of a wafer external view inspection apparatus is not fully utilized. This means that the execution of the wafer external view inspection is not necessarily easy and the inspection is not convenient. In addition, during the semiconductor inspection, an extremely large number of defects are detected when the process is started and, in some cases, more than hundreds of thousands of defects are detected. In such a case, all defects cannot be checked. When such a large number of defects are detected, it is very important to create a recipe so that those defects can be efficiently fed back to the semiconductor fabrication process.

SUMMARY OF THE INVENTION

It is an object of the present invention to provide a pattern inspection apparatus that can check defects efficiently and quickly even when a large number of defects are detected. It is another object of the present invention to provide a pattern inspection apparatus that can feed back the information, collected by the efficient defect checking, to the recipe data so that abnormal conditions can be detected quickly and correctly even when the inspection is carried out in the production line.

The pattern inspection apparatus according to the present invention combines a defect distribution map, a defect image list, a defect information list, and a defect information graph to achieve the objects described above.

A pattern inspection apparatus according to the present invention comprises substrate holding means for holding a substrate on which a pattern is formed; application means for applying a beam or a charged particle beam to the substrate held by the substrate holding means; detection means for detecting a signal generated from the substrate by the application; storage means for imaging and storing the signal detected by the detection means; comparison means for comparing the image stored in the storage means with an another image formed from a pattern identical in design; determination means for determining if defects are detected in the pattern based on the comparison result of the comparison means; display means having a map display part where positions of defects on the substrate are displayed as a map, an image display part where defect images are displayed, a list display part where a list of defect information is displayed, and a graph display part where statistical information on selected defect items is displayed as a graph; and area selection means for selecting an area included in the map displayed in the map display part, wherein, when a map area is selected by the area selection means, a list of defect images of defects in the selected map area is displayed in the image display part, a list of defect information on defects in the selected map area is displayed in the list display part, and/or a graph of statistical information on defects in the selected map area is displayed in the graph display part. The area selection means allows the user to select a map area through dragging or chip selection.

The pattern inspection means according to the present invention further comprises means for setting at least a classification code and a clustering group for defects selected from a wafer map through dragging or chip selection; means for creating filter information from at least the classification code or the clustering group that has been set; and means for registering the created filter into a recipe.

The present invention significantly improves the classification code setting function and the clustering setting function of an inspection apparatus and provides a practical, easy-to-use pattern inspection apparatus that allows the user to check defects and create a recipe.

Other objects, features and advantages of the invention will become apparent from the following description of the embodiments of the invention taken in conjunction with the accompanying drawings.

BRIEF DESCRIPTION OF THE DRAWINGS

FIGS. 9A, 9B are diagrams showing the relation of the map drawing mode and the map operation.

FIG. 14 is a diagram showing an example of a confirmation screen for confirming a display filter entered into the map.

FIG. 18 is a diagram showing the processing flow of a defect image sample condition.

DETAILED DESCRIPTION OF THE EMBODIMENTS

An embodiment of an inspection method and an inspection apparatus according to the present invention will be described in detail with reference to the drawings. The pattern inspection apparatus uses a beam, a laser beam, or a charged particle beam to measure the size of, observe, and inspect the external view of, a pattern formed on a semiconductor wafer.

Figure 1:
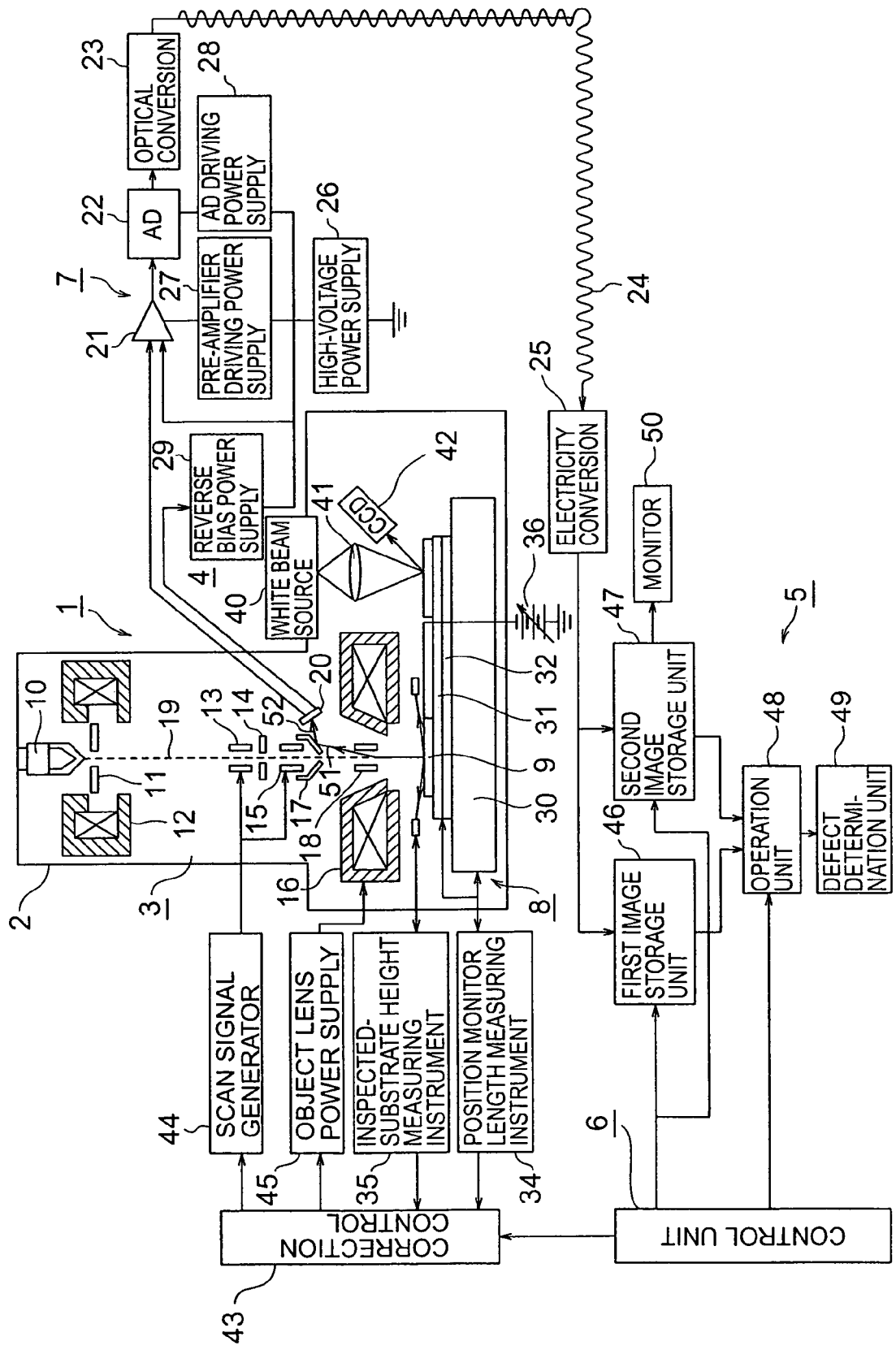
FIG. 1 is a general configuration diagram showing an example of a pattern inspection apparatus according to the present invention.
Figure 2:
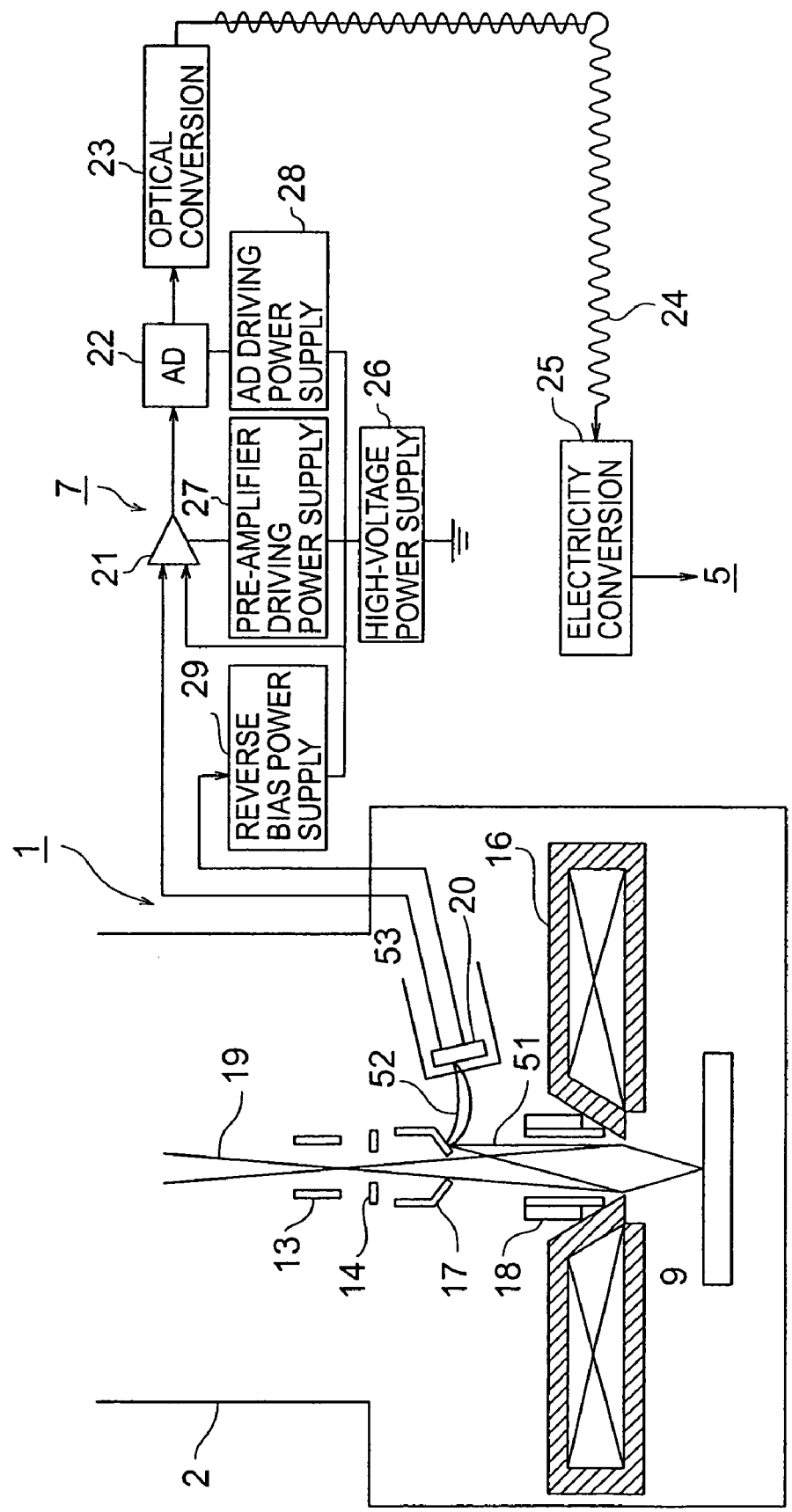
FIG. 2 is a diagram showing an enlarged illustration of an object lens shown in FIG. 1.

FIG. 1 is a general configuration diagram showing an example of a pattern inspection apparatus of the present invention, and FIG. 2 is a diagram showing an enlarged illustration near the object lens. A pattern inspection apparatus 1 shown in FIG. 1, which uses an electron beam, comprises an inspection room 2 that is vacuumed and a spare room (not shown in this embodiment) that is used for conveying an inspected-substrate 9 into the inspection room 2. This spare room is configured so that it can be vacuumed independently of the inspection room 2. In addition to the inspection room 2 and the spare room described above, the pattern inspection apparatus 1 further comprises a control unit 6 and an image processing unit 5. The inspection room 2 comprises roughly of an electronic optical system 3, a secondary electron detection unit 7, a sample room 8, and an optical microscope unit 4. The electronic optical system 3 comprises an electron gun 10, an electron beam induction electrode 11, a capacitor lens 12, a blanking polarizer 13, a scanning polarizer 15, an aperture 14, an object lens 16, a beam reflector 17, and an ExB polarizer 18. A secondary electron detector 20, one of the components of the secondary electron detection unit 7, is provided above the object lens 16 in the inspection room 2. The output signal of the secondary electron detector 20 is amplified by a preamplifier 21 provided outside the inspection room 2 and is converted to digital data by an AD converter 22. The sample room 8 comprises a stage 30, an X-stage 31, a Y stage 32, a rotary stage 33, a position monitor length measuring instrument 34, and an inspected-substrate height measuring instrument 35. The optical microscope unit 4 is positioned near the electronic optical system 3 in the inspection room 2, and they are provided apart in such a way they do not affect each other. The distance between the electronic optical system 3 and the optical microscope unit 4 is a known distance. The X-stage 31 and the Y stage 32 move back and forth between the electronic optical system 3 and the optical microscope unit 4 for the known distance. The optical microscope unit 4 comprises a beam source 40, an optical lens 41 and a CCD camera 42.

The image processing unit 5 comprises a first image storage unit 46, a second image storage unit 47, an operation unit 48, and a defect determination unit 49. A captured electron beam image or an optical image is displayed on a monitor 50. An operation instruction and an operation condition to be passed to the components of the apparatus are entered from the control unit 6. The conditions, such as the accelerating voltage at an electron beam generation time, the electron beam polarization width, the polarization speed, the signal capture time of the secondary electron detection device, and the stage movement speed, are entered into the control unit 6 to allow those condition to be set arbitrarily or selectively according to the purpose. The control unit 6 uses a correction control circuit 43 to monitor the difference in the position and the height from the signal received from the position monitor length measuring instrument 34 and the inspected-substrate height measuring instrument 35. Based on the result, the control unit 6 generates a correction signal and sends the correction signal to an object lens power supply 45 and a scan signal generator 44 so that the electron beam always strikes the correct position. To acquire an image of the inspected-substrate 9, a narrowed primary electron beam 19 is directed to the inspected-substrate 9 to generate a secondary electron 51. This secondary electron beam is detected in synchronization with the scanning of the primary electron beam 19 and with the movement of the stages 31 and 32 to give the image of the surface of the inspected-substrate 9.

High inspection speed is essential to automatic inspection. Therefore, unlike a standard SEM (Scanning Electron Microscope), a low speed scan with an electron beam of a pA-order electron beam current, a multiple-scan operation, or image overlapping is not carried out for automatic inspection. In addition, to prevent an insulating material from being charged with electricity, an electron beam scan must be made at a high speed only once or a few times at most. To meet this need, the apparatus in this embodiment forms an image by only one large-current electron beam scan, for example, 100 nA, that is about 100 times or larger than that of a standard SEM. The scanning width is 100 μm, one pixel is 0.1 μm□, and one scan is made in 1 μs.

A diffusion/re-supply type thermal field-emission electron source is used for the electron gun 10. As compared with a conventional tungsten (W) filament electron source or a cold field-emission electron source, this electron gun 10 supplies a stable electron beam current and therefore gives an electron beam image with a smaller brightness variation. In addition, the electron gun 10, which allows a large electron beam current to be set, can make a high-speed inspection as will be described later. The primary electron beam 19 is induced from the electron gun 10 by applying voltage across the electron gun 10 and the electron beam induction electrodes 11. The primary electron beam 19 is accelerated by applying a large negative potential to the electron gun 10. This causes the primary electron beam 19 to be supplied into the direction of the stage 30 with an energy corresponding to the potential. After converged by the capacitor lens 12 and narrowed by the object lens 16, the primary electron beam 19 is directed to the inspected-substrate 9 (semiconductor wafer, chip, or substrate having micro-patterns such as liquid crystals or masks) mounted on the X-Y stages 31 and 32 on the stage 30. The scan signal generator 44, which generates the scan signal and the blanking signal, is connected to the blanking polarizer 13, and the lens power supply 45 is connected to the capacitor lens 12 and the object lens 16, respectively. A negative voltage can be applied to the inspected-substrate 9 by a retarding power supply 36. By adjusting the voltage of the retarding power supply 36, the primary electron beam can be decelerated and the electron beam exposure energy applied to the inspected-substrate 9 can be adjusted to an optimum value without changing the potential of the electron gun 10.

The secondary electron 51, generated by directing the primary electron beam 19 to the inspected-substrate 9, is accelerated by a negative voltage applied to the inspected-substrate 9. The ExB polarizer 18, provided above the inspected-substrate 9, polarizes the accelerated secondary electron 51 into a predetermined direction. The amount of polarization can be adjusted by the intensity of the voltage and the magnetic field applied to the ExB polarizer 18. This electromagnetic field can be changed according to the negative voltage applied to the sample. The secondary electron 51 polarized by the ExB polarizer 18 conflicts with the beam reflector 17 under a predetermined condition. This beam reflector 17 is a cone-shaped reflector integrated with the shield pipe of the polarizer of the electron beam (called primary electron beam) directed to the sample. When the accelerated secondary electron 51 conflicts with this beam reflector 17, a second secondary electron 52, with the energy of several volts to 50 e volts, is generated from the beam reflector 17.

The secondary electron detection unit 7 comprises the secondary electron detector 20 that is inside the vacuumed inspection room 2, and the preamplifier 21, the AD converter 22, optical conversion means 23, optical transmission means 24, electricity conversion means 25, a high-voltage power supply 26, a pre-amplifier driving power supply 27, an AD converter driving power supply 28, and a reverse bias power supply 29 that are outside the inspection room 2. As described above, the secondary electron detector 20, one of the components of the secondary electron detection unit 7, is provided above the object lens 16 in the inspection room 2. The secondary electron detector 20, preamplifier 21, AD converter 22, optical conversion means 23, pre-amplifier driving power supply 27, and AD converter driving power supply 28 are kept at a positive floating potential by the high-voltage power supply 26. The second secondary electron 52 generated by the conflict with the beam reflector 17 is introduced into the secondary electron detector 20 by this suction electric field. The secondary electron detector 20 is configured in such a way that, at the same time the primary electron beam 19 is scanned, the secondary electron detector 20 detects the second secondary electron 52, wherein the second secondary electron 52 is generated when the secondary electron 51, which is generated while the primary electron beam 19 is directed to the inspected-substrate 9, is accelerated and then conflicts with the beam reflector 17. The output signal of the secondary electron detector 20 is amplified by the preamplifier 21 installed outside the inspection room 2 and is converted to digital data by the AD converter 22. The AD converter 22 converts the analog signal, detected by the secondary electron detector 20, into the digital signal immediately after the analog signal is amplified by the preamplifier 21 and transmits the digital signal to the image processing unit 5. Because the detected analog signal is converted to a digital signal immediately after the analog signal is detected and then the resulting digital signal is transmitted, the digital signal has a transmission rate and a S/N ratio higher than those of the conventional digital signal.

The inspected-substrate 9 is mounted on the X-y stages 31 and 32. One of two scanning methods can be selected; in one method, the X-y stages 31 and 32 are put in the stationary state at inspection time with the primary electron beam 19 scanning two-dimensionally and, in the other method, the X-y stages 31 and 32 are moved continuously in the Y direction at a constant speed with the primary electron beam 19 scanning linearly in the X direction. The former inspection method in which the stages are put in the stationary state is efficient for inspecting a relatively small area, and the latter inspection method in which the stages are moved continuously at a constant speed is efficient for inspecting a relatively large area. To blank the primary electron beam 19, the blanking polarizer 13 can be used to polarize the primary electron beam 19 so that the electron beam will not pass through the aperture 14.

In this embodiment, a length measuring instrument using laser interference is used as the position monitor length measuring instrument 34. With this measuring instrument, the position of the X-stage 31 and the Y stage 32 can be monitored in real time, and the measurement result can be transferred to the control unit 6. Data on the number of rotations of the X-stage 31, the Y stage 32, and the rotary stage can also be transferred from the drivers to the control unit 6. Based on the received data, the control unit 6 can correctly keep track of the area and the position in which the primary electron beam 19 is directed and, as necessary, uses the correction control circuit 43 to correct, in real time, a position error in the position in which the primary electron beam 19 is directed.

For each inspected substrate, an area in which the electron beam is directed can be stored. The inspected-substrate height measuring instrument 35, which employs an optical measuring instrument using a non-electron-beam measurement method, such as a laser interference measuring instrument or a reflected beam measuring instrument that measures a change in the reflected beam position, measures the height of the inspected-substrate 9 loaded on the X-y stages 31 and 32 in real time. In this embodiment, a fine white beam passing through a slit is directed to the inspected-substrate 9 through the transparent window, and the position detection monitor detects the position of the reflected beam to calculate the amount of change in the height from the change in the position. Based on the measurement data obtained by the inspected-substrate height measuring instrument 35, the focal length of the object lens 16 for reducing the amount of primary electron beam 19 is dynamically corrected to allow the primary electron beam 19 to be directed with the inspection area always in focus. In addition, it is also possible to measure a warp or a height distortion in the inspected-substrate 9 in advance before applying an electron beam and, based on the obtained data, to set a correction condition of the object lens 16 for each inspection area.

The image processing unit 5 comprises the first image storage unit 46, second image storage unit 47, operation unit 48, defect determination unit 49, and monitor 50. The image signal of the inspected-substrate 9 detected by the secondary electron detector 20 described above is amplified by the preamplifier 21, converted to a digital signal by the AD converter 22, converted to an optical signal by the optical conversion means 23, transmitted by the optical transmission means 24, converted back to an electrical signal by the electricity conversion means 25, and stored in the first image storage unit 46 or the second image storage unit 47. The operation unit 48 performs various types of image processing, for example, the positional alignment of the stored image signal with the image signal in another storage unit, the normalization of signal levels, and noise signal elimination, and compares both image signals. The defect determination unit 49 compares the absolute value of the difference image signal, produced as the result of the comparison operation by the operation unit 48, with a predetermined threshold value and, if the difference image signal level is higher than the predetermined threshold value, determines that the pixel is a defect candidate and displays the position and the number of defects on the monitor 50.

Figure 4:
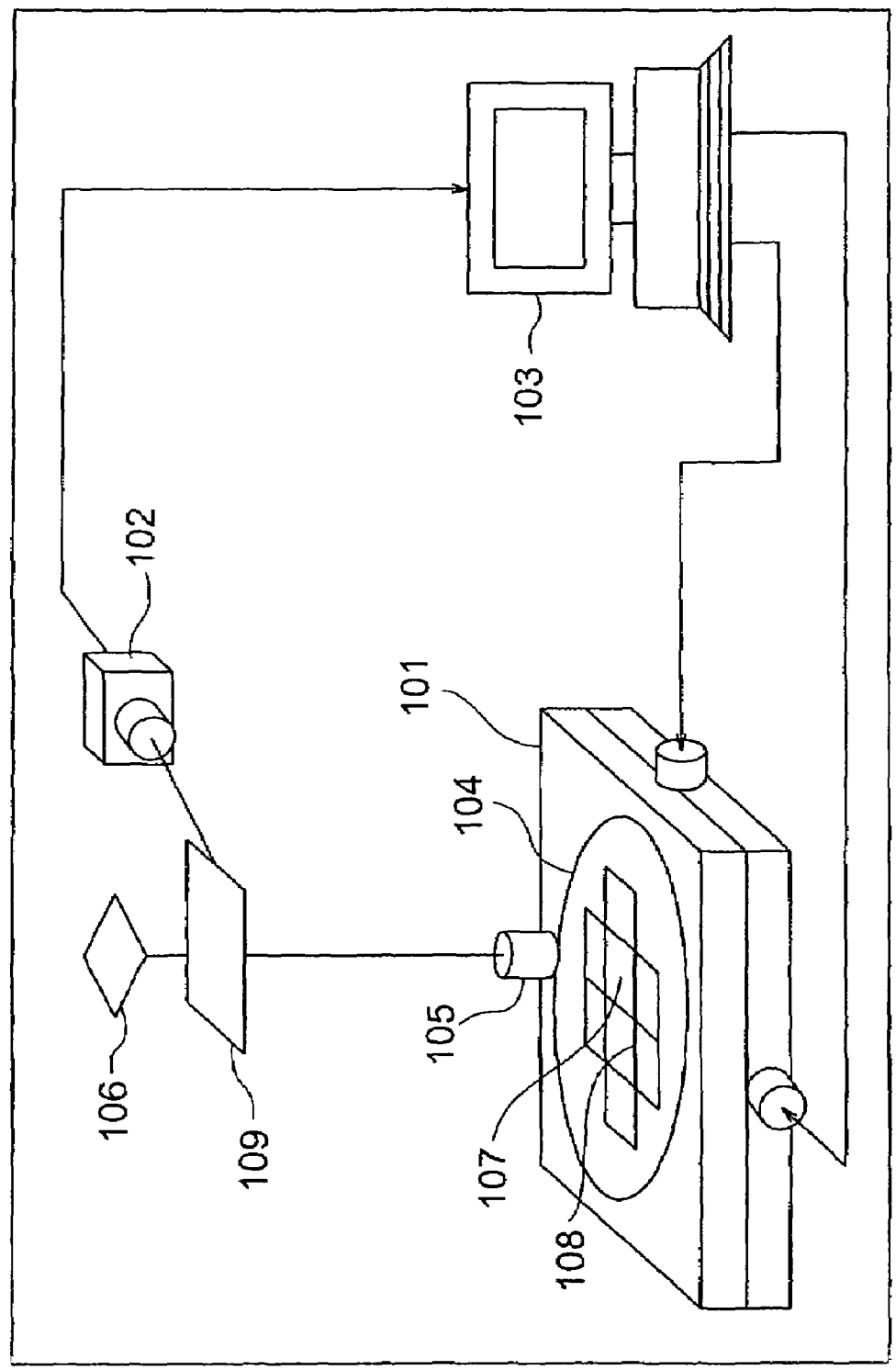
FIG. 4 is a block diagram showing the general configuration of a wafer external view inspection apparatus in one embodiment of the present invention.

Next, the following describes the general configuration of a wafer external view inspection apparatus that uses a beam or a laser beam as the beam source. FIG. 4 is a block diagram showing the general configuration of the wafer external view inspection apparatus in one embodiment of the present invention. An inspected wafer 104 is loaded on an X-Y stage 101. Chips are arranged in a regular grid on the inspected wafer 104. A control unit 103 moves the X-Y stage 101, an integral multiples of the chip pitch at a time. The beam from a beam source 106 is directed to the inspected wafer 104. The beam reflected on the inspected wafer 104 is passed through an object lens 105, split by a half mirror 109, and detected by a CCD camera 102 as a two-dimensional image.

The control unit 103 moves the X-Y stage 101 for one chip pitch to obtain the images of an inspected chip 107 and a comparison chip 108 in the same point. If the shading difference between the inspected chip 107 and the comparison chip 108 in the same point is larger than a predetermined threshold value, the control unit 103 determines that the inspected inspection chip 107 has a defect in the inspected point.

Figure 3:
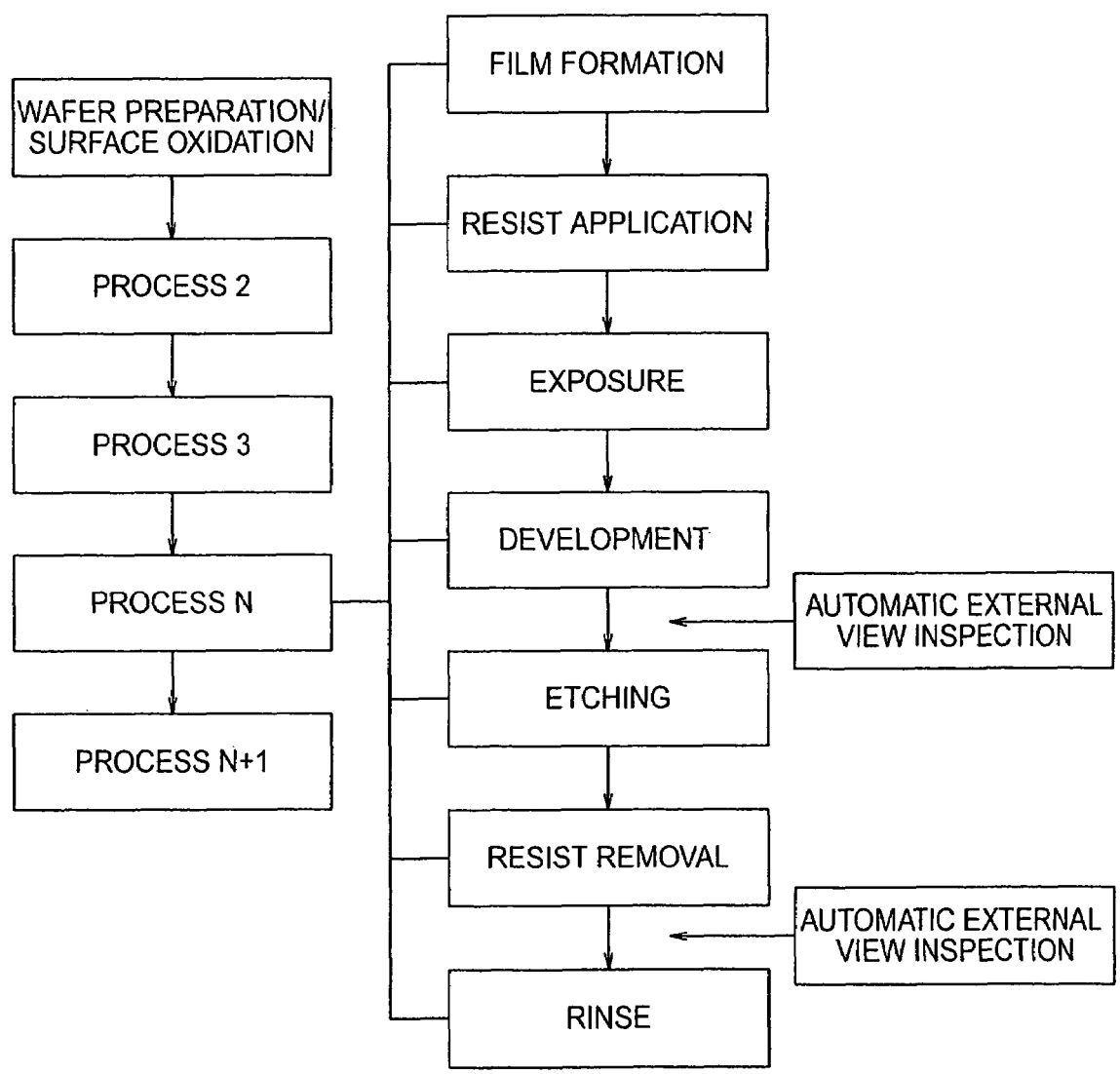
FIG. 3 is a diagram showing the fabrication process of semiconductor devices.

Next, the following describes an example in which the pattern inspection apparatus is applied to the inspection of a semiconductor wafer. FIG. 3 is a diagram showing the fabrication process of a semiconductor device. As shown in FIG. 3, a semiconductor device is fabricated by repeating many pattern formation processes. The pattern formation processes are composed roughly of the following steps: film formation/exposure, photo resist application, exposure, development, etching, resist removal, and rinse. Unless the processing fabrication condition is optimized in the steps, the circuit pattern on a semiconductor device cannot be formed on the substrate correctly.

For example, when an abnormal condition occurs during the film formation step in FIG. 3, a particle is generated and adhered to the surface of the semiconductor wafer with the result that an isolated defect is developed. If the conditions such as the focal point or the exposure time of the photolithography machine are not optimal for the exposure at exposure time, the amount of beam directed to the resist is too large or too small in a part and this uneven amount of beam sometimes causes a short, a broken line, and a thin pattern. If there is a defect in the mask reticle at exposure time, the same abnormal pattern shape is generated in the same position for a shot that is one unit of exposure. If the etching amount is not optimized or if a thin film or a particle is generated during etching, a short, a projection, an isolated defect, or an improper opening is generated. At rinse time, a fine particle is generated by impure water in the rinse tank or by the attachment of a flaked film or a foreign matter. In addition, if the drying condition is not good at drying time, the thickness of the oxide film on the surface tends to be irregular.

Therefore, the occurrence of an abnormal condition can be detected accurately and speedily during the fabrication process by inspecting a pattern formed on a semiconductor device and, based on the inspection result, a corrective action can be taken for the abnormal condition in the process to optimize the fabrication condition for preventing the defective from being developed. For example, if the circuit pattern inspection process, executed after the development process, detects a photo-resist pattern defect or a line disconnection, it is estimated that the exposure condition or the focal point condition of the photolithography machine in the exposure process is not optimized. Such a condition, if detected, can be improved quickly by adjusting the focal point condition or the exposure amount. A check is also made to determine if the defect distribution indicates whether those defects are generated in all shots and, if so, it is estimated that the photo-mask reticle used for pattern formation defective. If such a condition is detected, the photo-mask reticle should be inspected or exchanged as soon as possible. The same inspection method can be used for other processes. Executing the inspection process of a circuit pattern allows the user to detect various types of defects, and the detected defect contents allows the user to estimate the cause of an abnormal condition in each fabrication process.

An inline pattern inspection executed during the fabrication of semiconductor devices notifies the user about a change in the fabrication conditions or the occurrence of an abnormal condition during the inspection time and, thus, keeps the generation of defects to a minimum. In addition, information on the level of detected defects or the generation frequency of defects can be used to estimate the ratio of non-defective semiconductor devices to all fabricated semiconductor devices. This estimation can increase the semiconductor device productivity.

Figure 5:
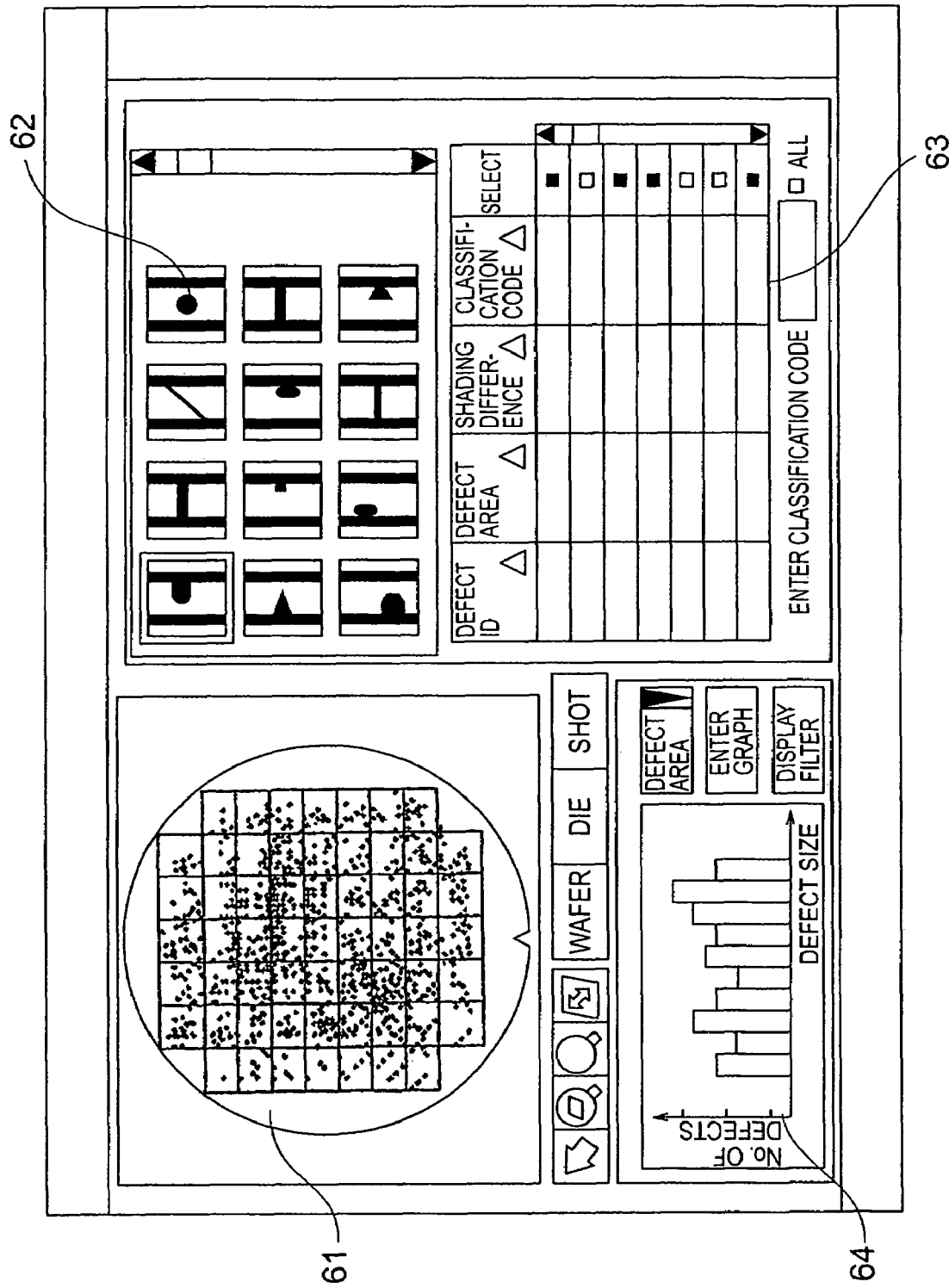
FIG. 5 is a diagram showing an example of a defect confirmation screen.

FIG. 5 is a diagram showing an example of the defect confirmation screen displayed on the monitor 50 shown in FIG. 1. The defect confirmation screen has four display parts. The first part is a "map display part" 61 where the map of a wafer and a die is displayed. The second part is an "image display part" 62 where the images of defects selected from the map are displayed. The third part is a "list display part" 63 where the list of defect information selected from the map is displayed and the defect information is set. The fourth part is a "graph display part" 64 where statistical information on the various defect items of the defects selected from the map is displayed as a graph. The display contents of the display parts 61-64 vary as the user performs operation in each display part, thereby enabling the user to check defects and to create a recipe quickly and easily.

First, the following describes a recipe necessary for inspecting a wafer. A recipe refers to a collection of data for inspecting a wafer. For example, the product class is 64M-DRAM and the process is LINE. This indicates that the product class is a kind of 64M memory and the process is a recipe for transferring wiring.

Figure 6:
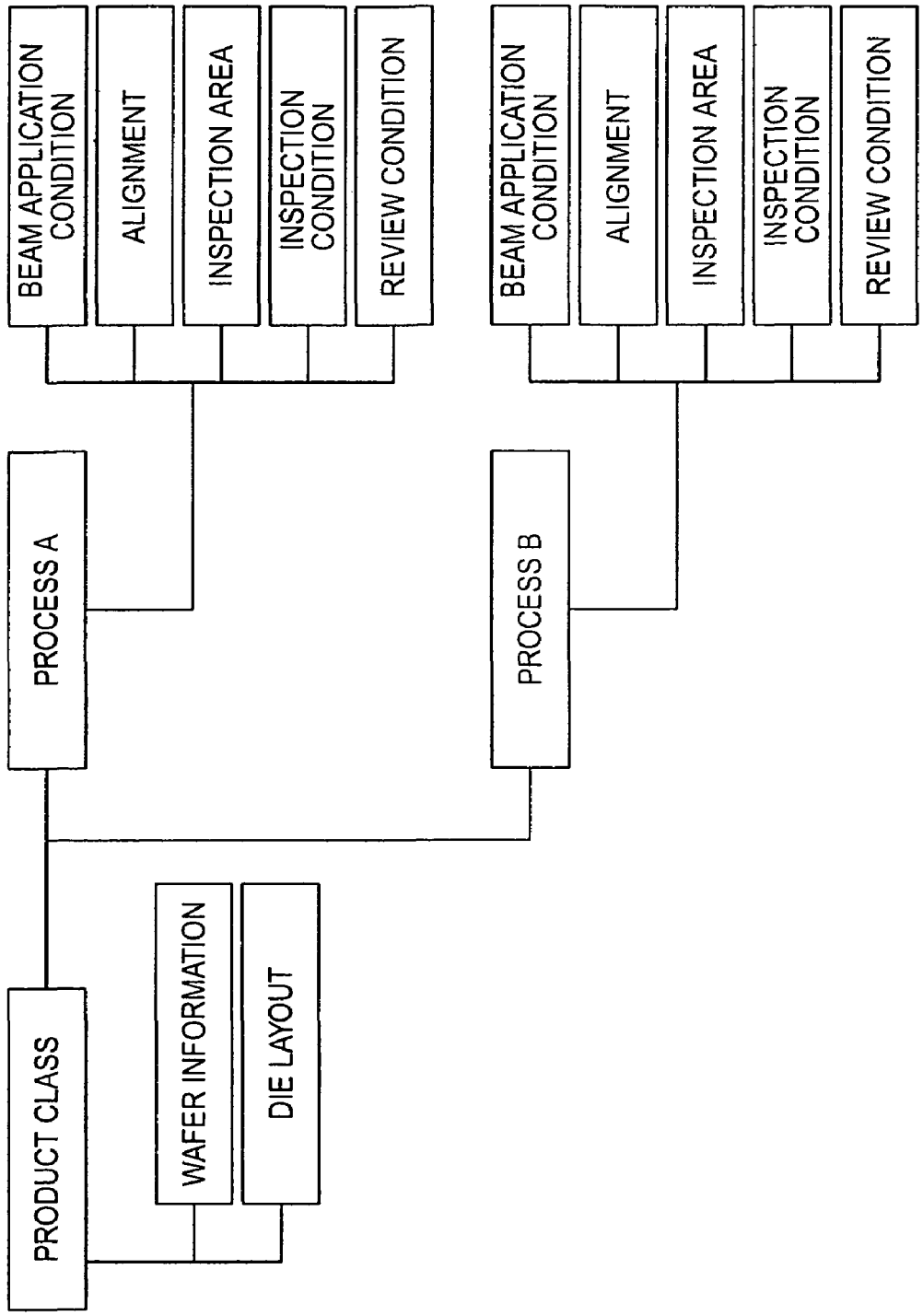
FIG. 6 is a diagram showing an example of the configuration of recipe data.

FIG. 6 shows an example of data configuration of a recipe. As an example, the product class data and the process data are hierarchically structured. The product class data is "wafer information" and "die layout". The "wafer information" is information such as the wafer diameter and the wafer type (orientation flat type or notch type). The "die layout" is information on the wafer transfer unit indicating the shot size, the number of shots, the size of the die in the shot, and the number of dies.

Next, the following shows an example of process data. The process data includes "beam application condition", "alignment", "inspection area", "inspection condition", and "review condition". The "beam application condition" indicates the retarding voltage for the electron beam to be applied to the wafer. At inspection time, this voltage value is set to acquire an image. The "alignment" indicates correction data for correcting an error generated when the wafer is transported into the sample room. An example of correction data is a die number, alignment coordinates in the die layout, and die origin offset data. The "inspection area" indicates an area used for wafer inspection. For example, the area is managed by the coordinates of the start point and the end point of the area. The "inspection condition" indicates an image processing filter, threshold, and image brightness and contrast that are applied to the actual inspection. An example of the inspection condition is a smoothing filter for reducing the noise of an image at inspection time. The "review condition" indicates a condition for observing defects after the inspection. An example of the review condition is a beam application condition, a cluster condition, a defect classification condition, and filter condition for the observation.

The process data is linked structurally to a production class. For example, when a production class has process A and process B and when process B is read and the die layout is changed, the die layout of process A is also changed. On the other hand, when the alignment data of process B is changed (for example, the alignment die is changed), process A is not affected. This recipe structure allows the same process to be changed at the same time. In a structure in which each process data unit has product class data, each of process A and process B can have its own "wafer information" and "die layout" information to which a change is made independently.

Figure 7:
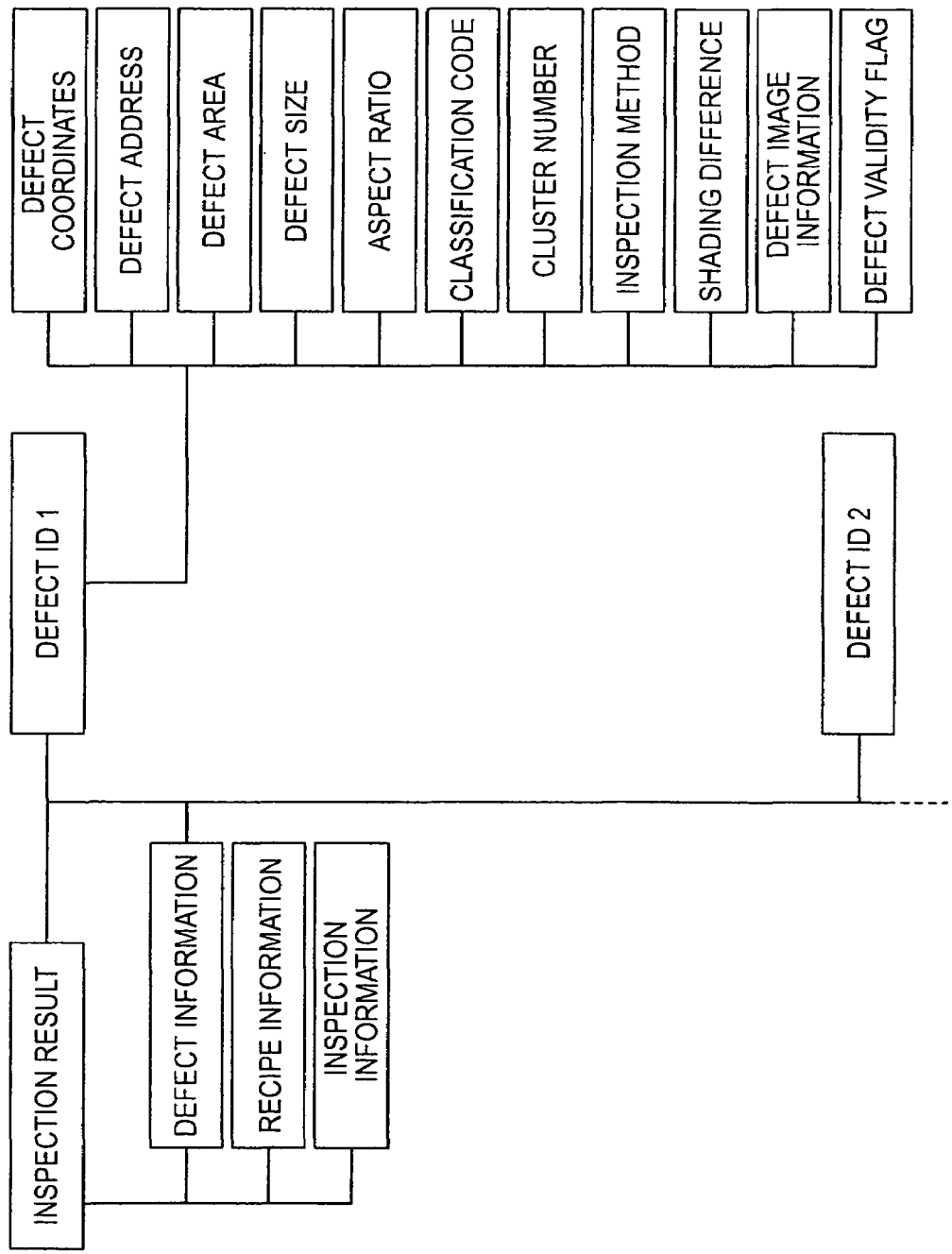
FIG. 7 is a diagram showing an example of the data configuration of inspection results and defect information.

Next, the following describes the data structure of the result of wafer inspection. This data structure is defined as "inspection result data". FIG. 7 shows an example of the data structure of inspection result and defect information. The inspection result data includes "defect information", "recipe information", and "runtime information". The "recipe information" indicates information on the recipe used for the inspection. As an example, the recipe information includes all data stored in the recipe.

The "inspection information" indicates various types of data generated by the wafer inspection. For example, the "inspection information" includes the number of defects, the defect density for the inspection area, the inspection time, and the inspection date and time of day. The "defect information" indicates defect data detected by the image processing apparatus by comparing the inspection data with the reference data. For example, the "defect information" includes the "defect coordinates", "defect address", "defect area", "defect size", "aspect ratio", "classification code", "cluster number", "inspection method", "shading difference", "defect image information", and "defect validity flag" all of which are related to the defect ID. There are three types of "defect coordinates": stage coordinates, in-die coordinates, and in-shot coordinates. The "defect address" indicates the die address and the shot address where the defect was detected. The "defect area" indicates the area of the defect. The "defect size" indicates the size of the defect in the X direction and the Y direction. The "aspect ratio" indicates the width-to-height ratio of the defect. There are two types of "classification codes": an automatic classification code and a manual classification code. The automatic classification code is a code classified according to the classification condition specified by the recipe. The "cluster number" is a number generated as a result of clustering according to the cluster condition specified by the recipe. The "inspection method" indicates an inspection method by which the defect was detected. When the defect was detected both by cell comparison and die comparison, the defect is treated as a mixed defect. The "shading difference" indicates the difference in brightness of the defect between the defect determination part and the reference part. For example, a black defect is a negative value and a white defect is a positive value. The "defect image information" is image information linked to the defect image. For example, the defect image address is set as the detect image information. The "defect validity flag" is information indicating whether the defect is valid or invalid. For example, if the user wants to display or select only a defect whose defect area is equal to or smaller than a predetermined value, the validity flag is turned off for a defect whose defect area is larger than the predetermined value.

The "map display part", "image display part", "list display part", and "graph display part" cooperate with each other based on the defect information selected in each display part.

Figure 8:
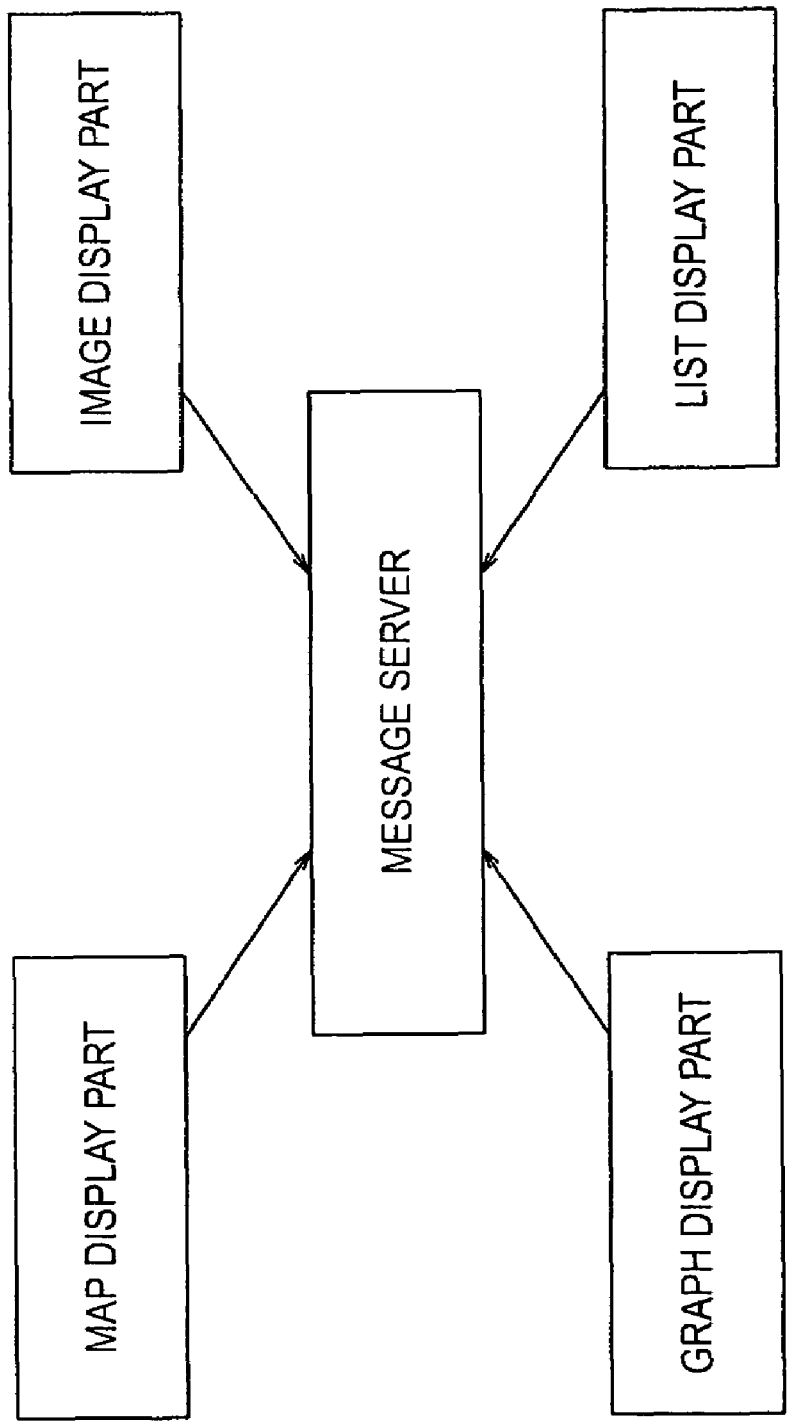
FIG. 8 is a diagram showing a relation among a map and other display parts.

For example, those display parts are implemented as a "map process", an "image process", a "graph process", and a "list process" which are independent of each other and have one shared defect information saving memory area as shown in FIG. 8. Of course, each process has its own defect information saving memory area. As an example of inter-process communication, the processes are connected by a message server. Each process is connected to the message server via a socket. Therefore, each process can be connected to the message server without worrying about other processes.

The user can also specify that one or more of the display parts be excluded from the cooperation with other parts. For example, if the user always wants to display all defects in the "list display part", the cooperation function can be turned off only for the "list display part". The size and the display position of each of those screens can be changed freely. For example, the user can drag the edge of each part to change the display size, and drag a display part to another position to change the display position in the screen. The changed size and position can be stored as the starting coordinates and size. The setting is effective at the next startup and can be reset to the default starting coordinates and size any time the user wants. The ability to freely change the screen size and the display position provides the user with an easy-to-use screen.

The following describes each screen part in detail. First, the "map display part" 61 will be described. In the "map display part", the whole wafer map is drawn based on the wafer information and the defect information. At least the wafer outline and the die are created based on the wafer information to build the whole wafer screen. In addition, the in-die inspection area, if drawn, could make the actually inspected area clearer. The drawn map has the following three major modes as shown in the map drawing mode shown in FIG. 9A.

(1) Mode for displaying whole wafer
(2) Mode for displaying one or more overlapped dies of the wafer
(3) Mode for displaying one or more overlapped wafer shots of the wafer The modes can be switched by the buttons. The display indicating which mode is currently used, if shown, makes the screen easier to use. In this example, (1) is assigned to the "Wafer" button, (2) is assigned to the "Die" button, and (3) is assigned to the "Shot" button. Those buttons may be changed to a combo box or radio buttons.

In addition, in each of the three map modes, the user can perform the following three types of operation as shown in FIG. 9B:

(1) Operation for selecting a defect in the map
(2) Operation for selecting a defect in an area in the map
(3) Operation for scaling an area in the map The operations can be switched by the buttons. The display indicating which map operation is currently executed, if shown, makes the screen easier to use. In this example, (1) is assigned to the "Arrow" button, (2) is assigned to the "Magnifying glass+Square" button, and (3) is assigned to the "Magnifying glass" button. Those buttons may be changed to a combo box or radio buttons. Combining the three map modes with the three operations makes the relation of the wafer map information and the defect information easier to understand. For example, if the user wants to observe multiple defects that which concentrate in a particular part of the wafer, all at a time, the user can select map mode (1) and map operation (2) to select all concentrated defects.

Figure 10:
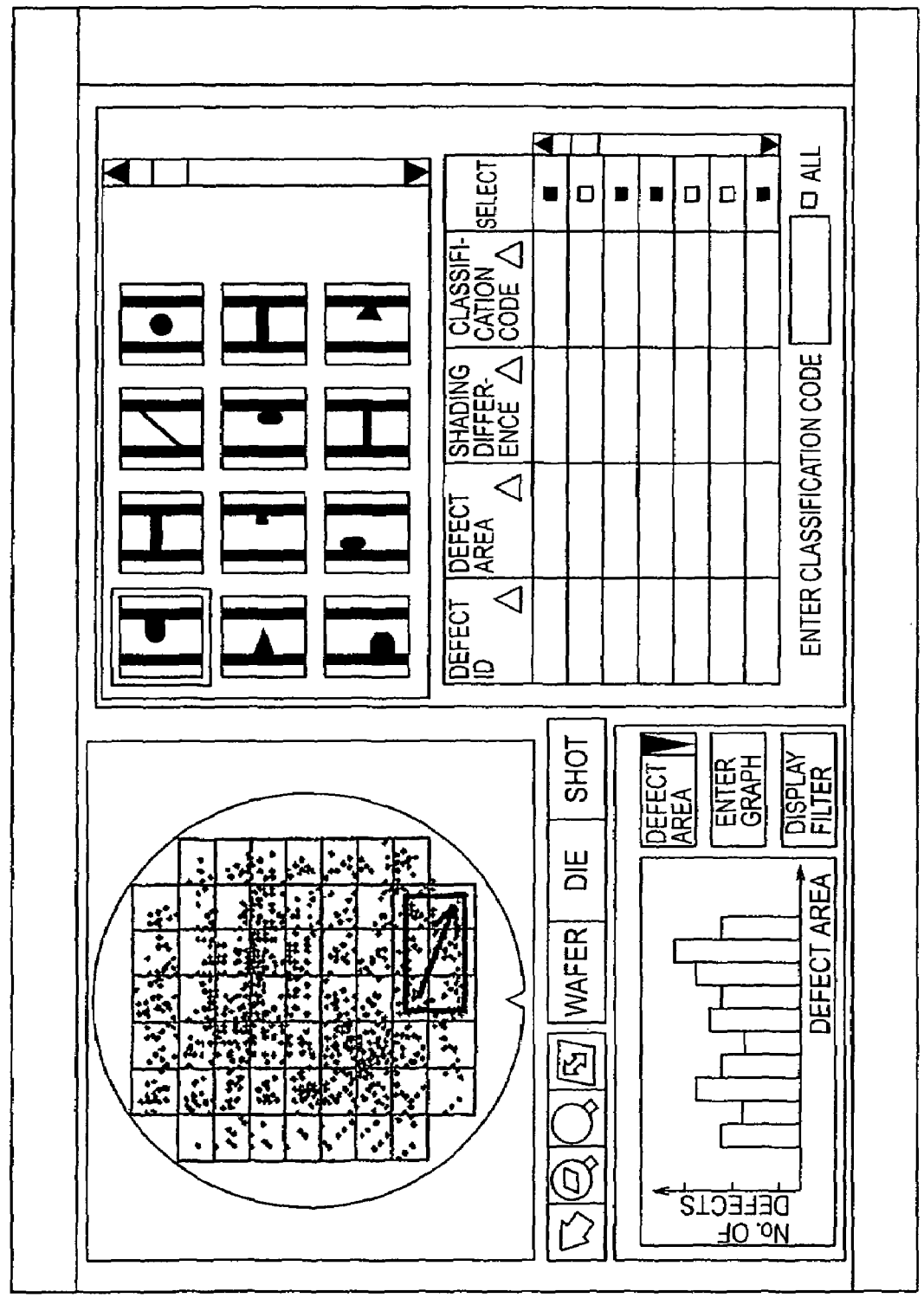
FIG. 10 is a diagram showing an example of area selection by entering a start point and an end point in the map.
Figure 11:
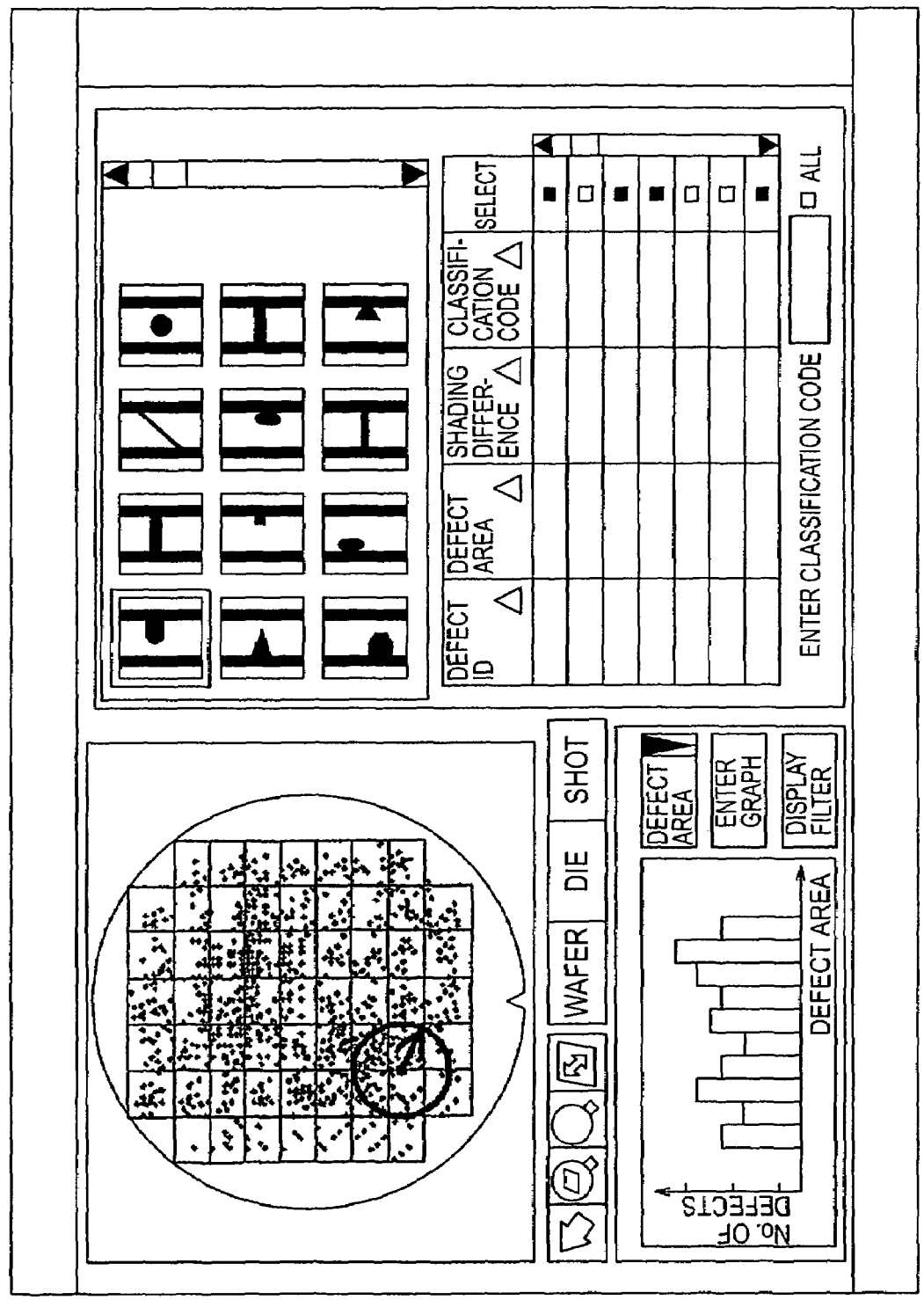
FIG. 11 is a diagram showing an example of area selection by entering a center and a radius in the map.
Figure 12:
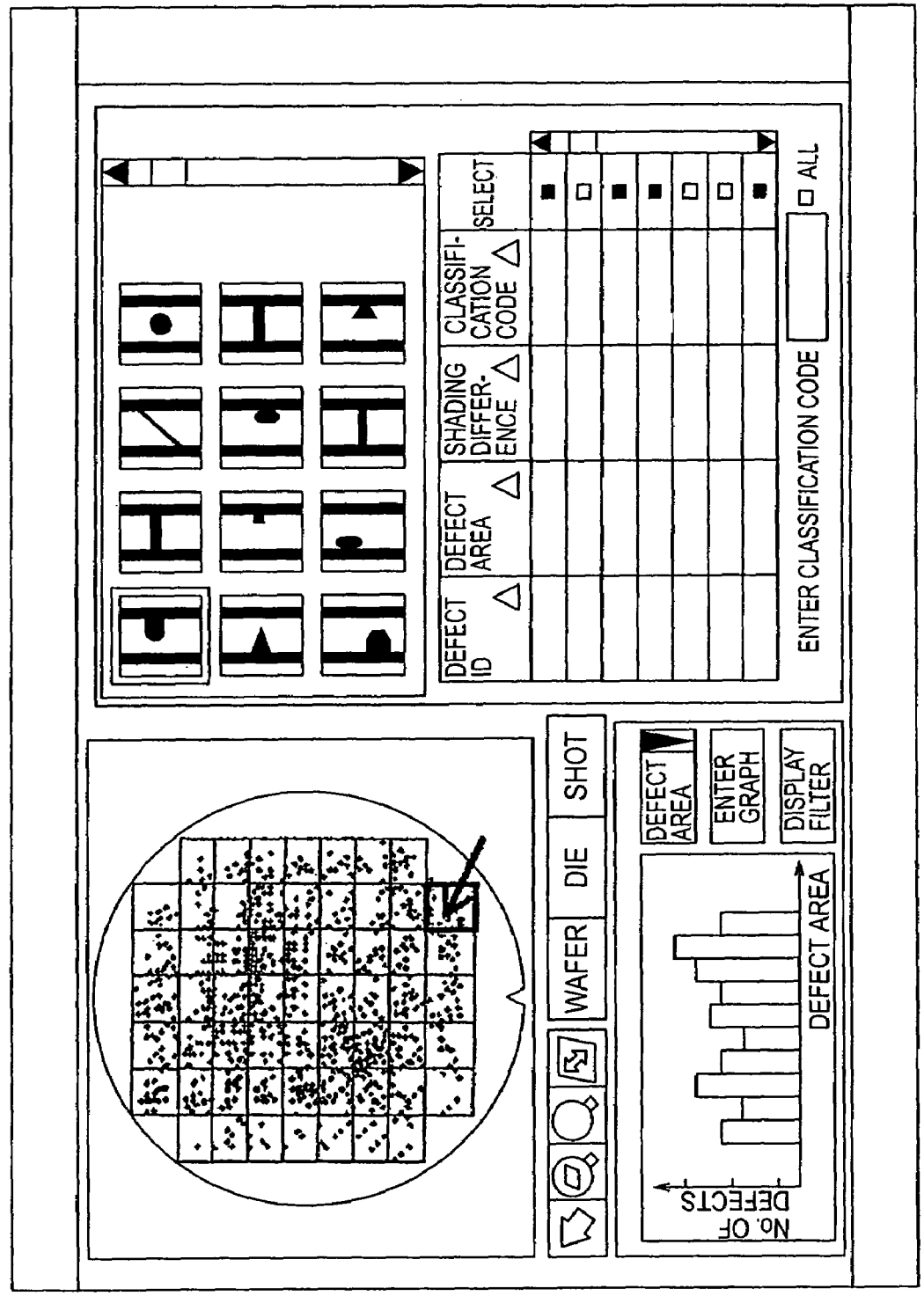
FIG. 12 is a diagram showing an example of area selection by specifying a die in the map.

The following three operations are available for the selection method of an area, shown in map operation (2), as shown in FIGS. 10, 11, and 12.

(1) Map drag operation by entering a start point and an end point
(2) Map drag operation by entering a center and a radius
(3) Map click operation by specifying a die The user specifies a start point and an end point in the map by dragging on the screen as shown in FIG. 10 to notify the defects in the selected area to the "image display part", "list display part", and "graph display part" for displaying the information on the defects in the area.

The user specifies a point and a radius in the map by dragging on the screen as shown in FIG. 11 to notify the defects in the selected area to the "image display part", "list display part", and "graph display part" for displaying the information on the defects in the area.

The user specifies a die in the map by clicking on it as shown in FIG. 12 to notify the defects in the selected die to the "image display part", "list display part", and "graph display part" for displaying the information on the defects in the die.

Next, the following describes the "image display part" 62. In the "image display part" 62, the image of at least one defect notified from the map is displayed. Any size of a display image can be specified, for example, by the number of pixels. Displayed images are those stored in the image processing unit (hereinafter called an inspection images). The images may be those output internally or externally during the inspection. An image re-acquired after the inspection can also be displayed. Because one image to hundreds of thousands of images can be displayed, the scrollbar can be provided to allow the user to move through the display part easily. Instead of the scrollbar, tabs can also be provided to allow the user to easily move through the display part.

When the user selects a defect displayed in the image display part, the selection is notified also to the "map display part", "list display part", and "graph display part". In response to the notification, the corresponding defect in the map is highlighted in the "map display part". In addition, in response to the notification, the information on the corresponding defect is highlighted in the "list display part". In addition, the component part of the graph, to which the corresponding defect belongs, is highlighted in the "graph display part". Instead of a highlight display, it is also possible to change the display color or to display a navigation line.

Next, the following describes the "list display part" 63. The function of the "list display part" is divided roughly into the following two functions:
(1) Function to display defect information list
(2) Function to add information to defects The function to display defect information list displays detailed information on at least one defect notified from the map display part. The user can select the detailed information items of the defects to be displayed. Because the display list can contain one entry to hundreds of thousands of entries, the toolbar can be provided to allow the user to move through the display part easily. Instead of the toolbar, tabs can also be provided to allow the user to easily move through the display part. By selecting items of the list, the list can be sorted in ascending order or descending order by the selected items. The "select" item is provided as a list item other than the defect information. When there is a setting item to be applied only to a part of the defects obtained from the map display part, this "select" checkbox can be used to apply information only to the defects checked by this "select" checkbox. For example, when a classification code is set at a time or a clustering group is set, it is sometimes desired to assign the same classification code and the clustering number to the defects other than specific defects. In such a case, this "select" item button is pressed to inactivate the sort function of the other defect information but to activate the all-select and all-deselect function.

The function to add information to defects adds at least one piece of information to the defects selected in the list. In the example shown in the figure, the classification code is added. Another example of information that is entered is marking information indicating a defect that is a point. After the classification code is assigned, the entry automatically changes to the next defect list entry and waits for the user to enter a classification code.

The user wants to specify a classification code individually for each item in some case while, in some other case, to specify the same code for all the selected defects. To meet this need, the function to specify a classification code for multiple defects at a time is provided. To specify a classification code at a time, the user checks the "All" checkbox and enters a classification code. Then, the entered classification code is assigned to all the "selected" defects.

When the user selects a defect from the displayed list, the selection is notified to the "map display part", "image display part", and "graph display part". In response to the notification, the corresponding defect is highlighted in the map in the "map display part". In addition, in response to the notification, the edge of the image of the corresponding defect is highlighted in the "image display part". In addition, the component part of the graph, to which the corresponding defect belongs, is highlighted in the "graph display part". Instead of a highlight display, it is also possible to change the display color or to display a navigation line.

Next, the following describes the "graph display part" 64. The function of the "graph display part" is divided roughly into the following two functions:
(1) Function to graphically display defect information
(2) Function to set a defect display filter for displayed map The function to graphically display defect information is used to display a graph with the axes of the graph indicating the specified defect information items and the number of displayed defects. A bar graph or a line graph can be displayed according to the user's selection. The defect information to be displayed in the graph can be specified by the combo box. The items that can be displayed are all defect information including "defect ID", "coordinates", "size", and "shading difference". Instead of the combo box, radio buttons or pre-set buttons can also be used to select defect information to be displayed. To scale the graph, the "Magnifying glass" button of the "map display part" can be used also in the "graph display part". The "Magnifying glass" button is used to scale a specific part of the graph. The scaled graph information is held until the next time the "Magnifying glass" button is pressed.

Figure 13:
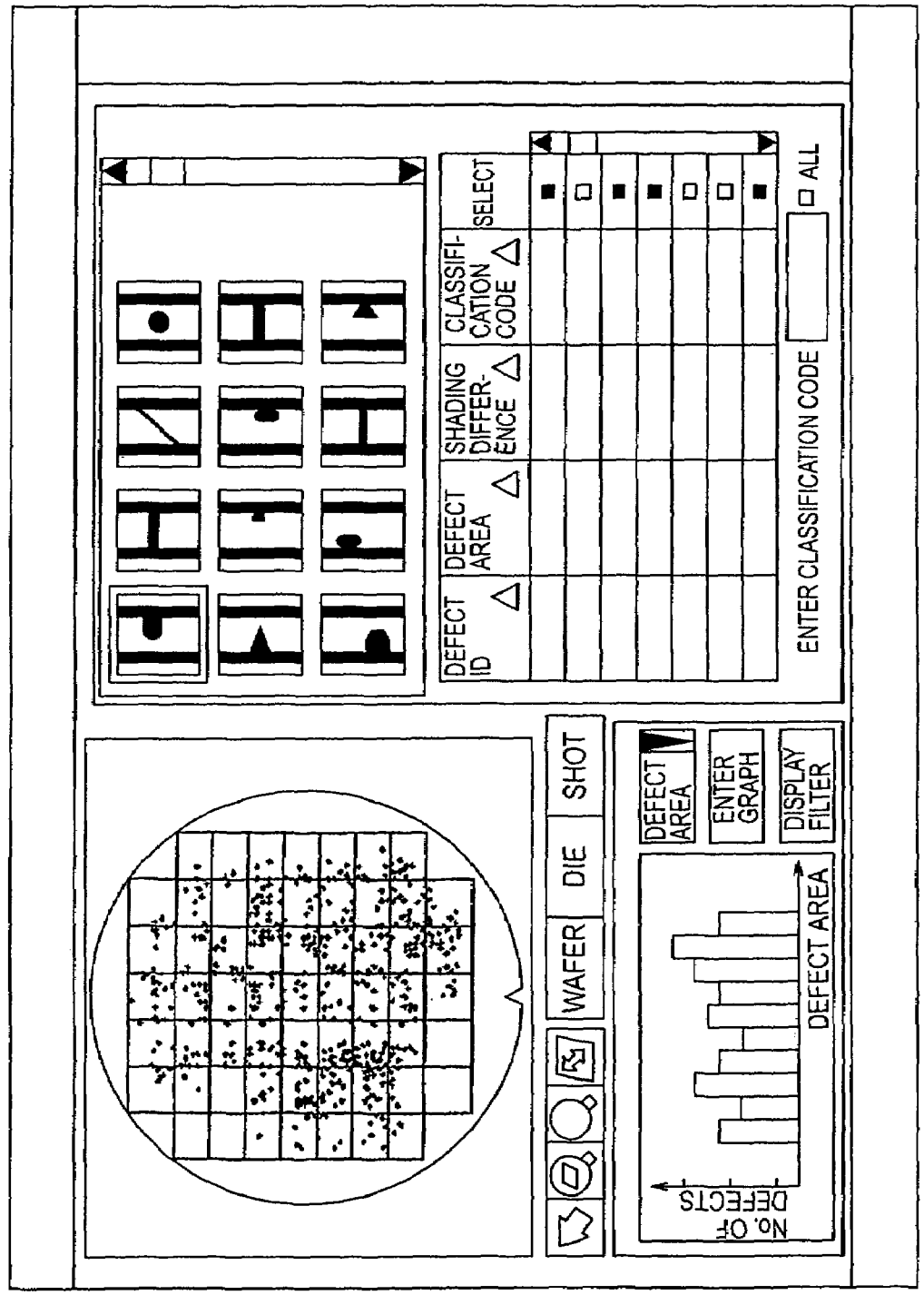
FIG. 13 is a diagram showing an example of the entry of a display filter into the map.

The function to set a defect display filter for the displayed map is used to set filtering information on the defects to be displayed in the map using the graph display function. This entry function allows the user to graphically enter filter information from a graph. When the "Enter graph" button is pressed, the user can enter the upper limit and the lower limit. As the user drags the upper and lower limits, the display in the "map display part" 61 is changed accordingly and the defect distribution is changed. The user enters the upper limit and the lower limit, for example, by clicking the right button of the mouse on the graph to set the upper limit, and the left button to set the lower limit, with the "Enter graph" button held. As shown in FIG. 13, the upper limit and lower limit boundary lines are drawn in the corresponding parts each time the user clicks the mouse. At the same time the upper and lower limits of the graph are set, the number of defects displayed in the "list display part" 63 is also changed.

The "Display filter" button can be used to confirm the executed filter condition. As shown in FIG. 14, a filter condition entered from the graph can be confirmed by the "Display condition dialog". This function allows the user to edit or re-execute a filter condition visually entered from the graph. This function also allows the user to display and execute a filter condition, which is difficult to enter from the graph, for more efficient execution of a display filter. For example, the user can specify two parameters, a radius and the number of elements, to set up a clustering condition. When there is a set of defects satisfying the specified cluster condition, that is, when there are defects, each of which has defects no fewer than the specified number of elements within the specified radius, within the distance of the specified radius from one particular defect that is the center, a cluster number is assigned to each of those defects. At this time, it is also possible to assign cluster numbers, one for each die, to a die, a shot, or a wafer by selecting the range where the defect search is made. In addition, by specifying two parameters, that is, in-die defect-to-defect distance or in-shot defect-to-defect distance and the number of elements, the same cluster number can be assigned to the reticle defects detected in the same die-coordinates or shot coordinates. That is, when there are defects, each of which has defects no fewer than the specified number of elements within the specified radius in the die coordinates or shot coordinates, within the distance of the specified radius from one particular defect that is the center, a cluster number is assigned to each of those defects.

The following describes the relation between actual defect data and the GUI. The cooperative operation among the four display pats is executed when the user performs operation in any of those display parts.

First, the cooperative operation started in the "map display part" is executed as follows. When the user selects a defect in the map, the map process notifies the selected defect ID to the "image process", "graph process", and "list process" via broadcasting or a file. The "map process", "image process", and "list process" highlight the notified defect ID. The "graph process" highlights the graph part to which the selected defect ID belongs.

Second, the cooperative operation started in the "image display part" is executed as follows. When the user selects a defect from the image display part, the image process notifies the selected defect ID to the "map process", "graph process", and "list process" via broadcasting or a file. The "map process", "image process", and "list process" highlight the notified defect ID. The "graph process" highlights the graph part to which the selected defect ID belongs.

Third, the cooperative operation started in the "list display part" is executed as follows. When the user selects a defect from the list display part, the list process notifies the selected defect ID to the "map process", "image process", and "graph process" via broadcasting or a file. The "map process", "image process", and "list process" highlight the notified defect ID. The "graph process" highlights the graph part to which the selected defect ID belongs.

Fourth, the cooperative operation started in the "graph display part" is executed as follows. When the user selects a defect from the graph display part, the graph process notifies all defect IDs corresponding to the selected graph display part to the "map process", "image process", and "list process" via broadcasting or a file. The "map process", "image process", and "list process" highlight all notified defect IDs. The "graph process" highlights the graph part to which the selected defect ID belongs.

The user can select multiple defects from the "map display part", "image display part", and "list display part". The following describes the relation among data in that case.

First, the selection of multiple defects from the "map display part" is triggered by the mouse drag operation in a part of the defect distribution map where multiple defects are included. An area can be selected by entering the "start point/end point" or "center/radius". When a defect selection area is created in the defect distribution map, the "map process" calculates the stage coordinates corresponding to the area and the number of the die including the area. For the defects in the die whose number is calculated, the map process calculates whether the defects are within the selected area based on the stage coordinates. The process notifies the IDs of defects, which are determined to be in the area, to the "image process", "list process", and "graph process" via broadcasting or a file. The "map process", "image process", and "list process" highlight all notified defect IDs. The "graph process" highlights the graph part to which the selected defect IDs belong. Instead of highlighting the graph part in the graph display part, it is also possible to change the color according to the number of notified defects corresponding to the graph or to provide an area within the graph display part where the number of selections is displayed.

Second, the selection of multiple defects from the "image display part" is triggered by the mouse drag operation, or by the mouse click operation with the Shift button and the Ctrl button held on the keyboard, in a part of the image list where multiple defects are included. Each time a defect selected from the image display part is updated, the defect ID is notified to the "map process", "list process", and "graph process". In response to the notification, the processes update the display based on the notified defect ID.

Third, the selection of multiple defects from the "list display part" is triggered by the mouse click operation, or by the mouse click operation with the Shift button and the Ctrl button held on the keyboard, in a part of the list where multiple defects are included. Each time a defect selected from the list display part is updated, the defect ID is notified to the "map process", "image process", and "graph process". In response to the notification, the processes update the display based on the notified defect ID.

Figure 15:
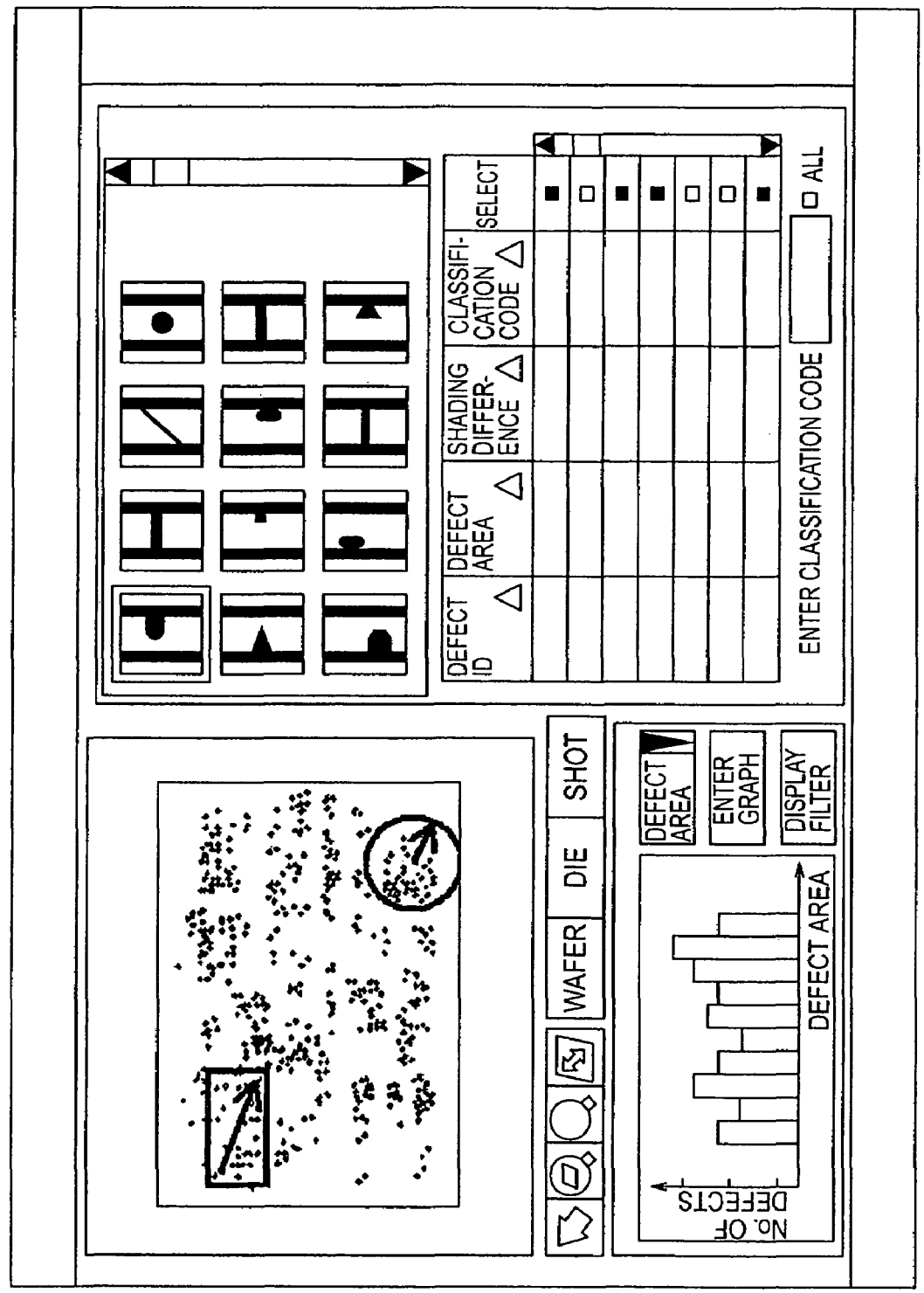
FIG. 15 is a diagram showing a die overlapping function screen in the map.
Figure 16:
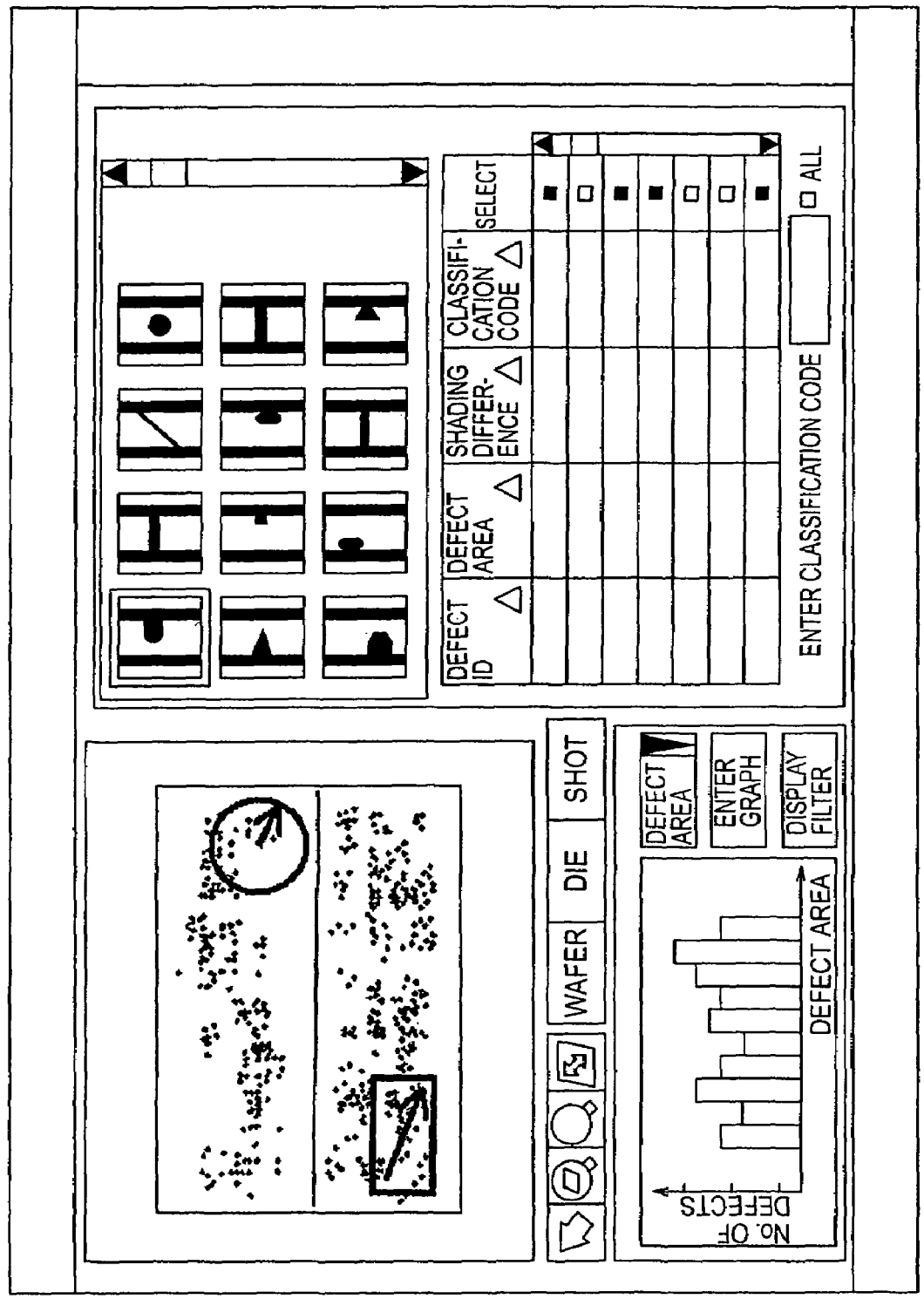
FIG. 16 is a diagram showing a shot overlapping function screen in the map.

The die overlap function and the shot overlap function in the defect distribution map are available as an extended function of defect confirmation. FIG. 15 shows a defect die map generated by overlapping all inspected dies using the in-die coordinates of the "defect coordinates" of the defect information. FIG. 16 shows a defect shot map generated by overlapping all inspected shots using the in-shot coordinates of the "defect coordinates" of the defect information. Although all dies and all shots are overlapped in those examples, it is also possible to create a defect map of only the selected dies and shots rather than all inspected dies and shots. Because one die is created in the X direction, and two dies in the Y direction, in one shot in the example shown in the figure, FIG. 16 shows the map of one shot (two dies). This overlap function allows the user to find the tendency and distribution of defects that are not found only by checking the wafer map and to easily detect the defects detected in the same area of different dies or different shots. The cooperative operation of the display parts using this die overlap function and the shot overlap function is the same as that for the normal defect distribution map.

The functions described above are efficient for the defect confirmation even after the execution of normal inspection and are more efficient for the defect confirmation screen during recipe creation.

During recipe creation, the information can be added to the recipe information by the following three automatic execution-processing functions that are executed after the inspection.

(1) Classification code assignment function using defect information
(2) Clustering function using defect coordinates
(3) Automatic filtering function First, the automatic classification code assignment function using defect information, the first function described above, is used to create an area (hereinafter called a classification area) where a user-entered defect classification code is assigned to as many defects as possible and to register the created classification area in the recipe.

Figure 17A:
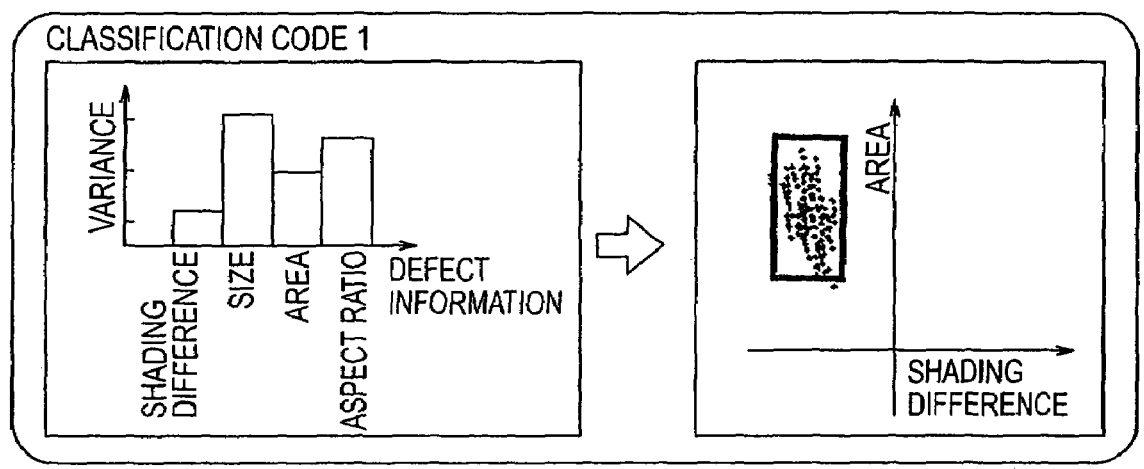
FIGS. 17A, 17B are diagrams showing an example of a classification method using defect information.
Figure 17B:
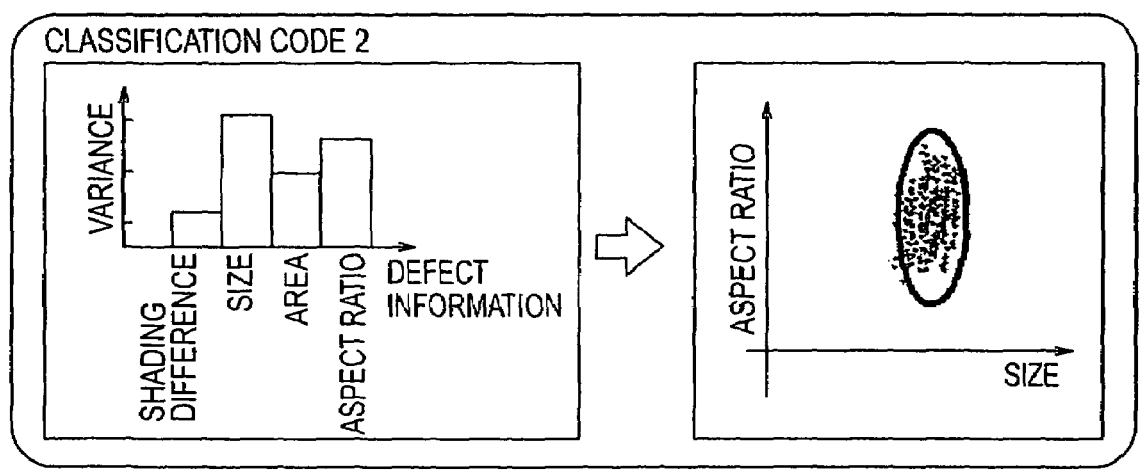

For example, when the characteristic defect information is "shading difference", "size", "area", and "aspect ratio (width-to-height ratio)" as shown in FIG. 17A, the "shading difference", "size", "area", and "aspect ratio" items of the defects assigned to the classification code 1 are added up and the variance of each item is calculated. After that, at least one item is automatically selected in ascending sequence of variances beginning with the lowest variance. In this example, two items are selected and the defects are classified two-dimensionally. A classification area is specified using a square or an ellipse so that the specified classification code 1 is assigned to more than the specified classification percent of the selected defects. The specified classification percent, which has the default value of $3\sigma$, is a parameter that can be changed. The classification area determined in this manner is registered in the recipe as the definition of the classification code 1 and, from this time on, the classification code 1 is automatically assigned to a defect that will belong to this area. The same processing is performed for the classification code 2 as shown in FIG. 17B to create a classification area. If multiple classification codes are assigned to a defect, the code is determined according to the predetermined classification code priority.

The user can graphically confirm and easily change those "classification areas" in the graph. To change a classification area, the user dynamically drags the line that forms the classification area of the graph displayed in the right half of FIG. 17A or FIG. 17B. The user can also specify classification code priority for each recipe and, in addition, can select a square for the shape of a classification area although the default is an ellipse. If "in-die coordinates" and "in-shot coordinates" are added to the axis components of this classification area, a "reticle defect" that may be detected in the same coordinates of other dies or in the same coordinates of other shots can also be recognized easily.

Next, the defect clustering function, the second function described above, is used to register a user-entered clustering condition into the recipe. The minimum number of defect elements of a clustering group and the defect-to-defect distance, which are entered by the user, are registered in the recipe as the clustering condition. The clustering condition may also be specified by entering the numeric values of the minimum number of elements (minimum number of defects constituting a cluster) and the element-to-element distance (defect-to-defect distance).

The filtering function, the third function described above, is used to register filtering information, entered by the user using the filter function shown in FIG. 13, into the recipe. The filter items that cannot be entered from the map are entered from the specified dialog. For example, the user uses this dialog to specify the items of a filter for randomly selecting only an arbitrary number of defects from an arbitrary number of defect IDs or the items of a filter for selecting only an arbitrary number of equally spaced defects from an arbitrary number of defect IDs. To positively distinguish a filter from that used temporarily for defect classification, the user is requested to perform operation with special awareness for recipe registration. For example, a dialog is displayed to ask the user after the defect confirmation whether to register a filter that is currently effective.

Those three processing functions are executed after the inspection to set up a hierarchically structured defect image sample condition in the recipe, as shown in FIG. 18, to help the user to check the defects highly efficiently after the inspection. This hierarchically structured defect image sample condition is used when the following are automatically set by the recipe as shown in FIG. 18: "classification code" information that is assigned automatically to a defect, which is plotted in a special area associated with some defect characteristics, based on the information shown in FIG. 17; "cluster number" that is assigned to each of the defects, each of which has defects not fewer than the specified number of elements within the specified radius, from one particular defect that is the center; and "defect validity flag" that is assigned for selecting only valid defects. For example, the hierarchically structured defect image sample condition described above is used to select only the defects with a particular classification code from cluster defects, to which a cluster number is assigned, based on the valid defects. It is possible to select only an arbitrary number of defects, which are to be observed or whose defect images are to be obtained, from the selected defects. Similarly, only those defects with no cluster number are selected from defects, to which a particular classification code is assigned, based on the valid defects. It is possible to select only an arbitrary number of defects, which are to be observed or whose defect images are to be obtained, from the selected defects. A hierarchically structured defect image sample condition like this can be used not only as an image sample condition but also in defect confirmation. Therefore, the condition is registered in the recipe and at the same time registered externally as a review condition file to allow the user to simply load it as a review condition when loading another recipe.

Figure 19A:
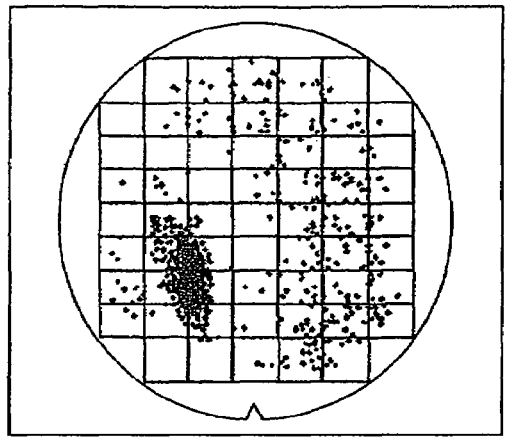
FIGS. 19A, 19B are diagrams showing an example of a defect distribution map after inspection.
Figure 19B:
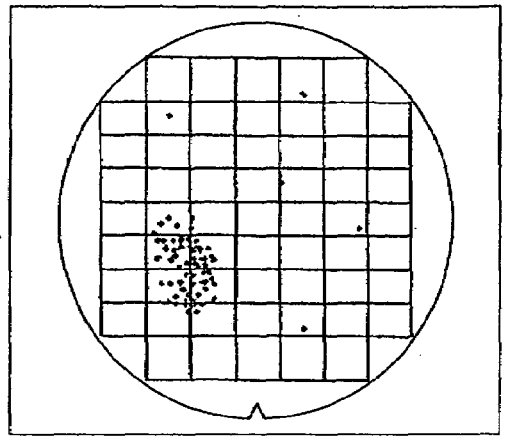
Figure 20A:
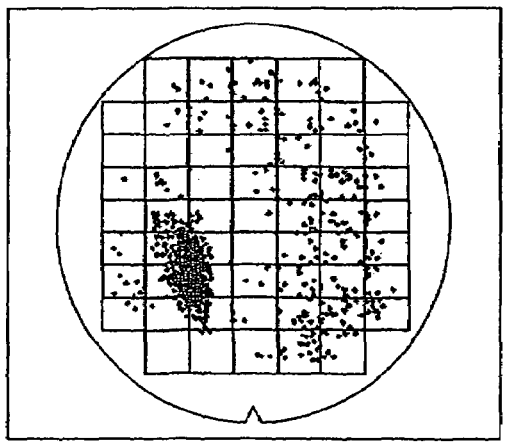
FIGS. 20A, 20B are diagrams showing an example of a defect distribution map after inspection.
Figure 20B:
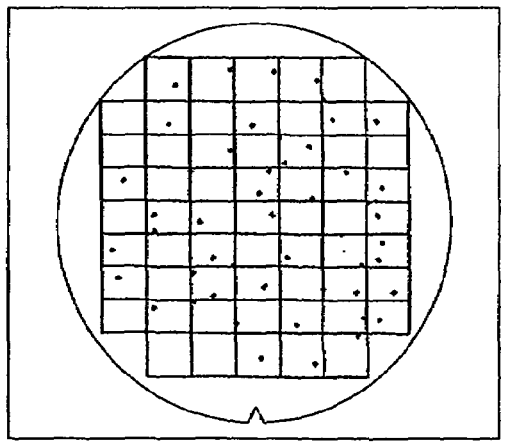

FIGS. 19A, 19B and FIGS. 20A, 20B show the defect distribution maps generated as a result of inspection using a recipe before the present invention is applied and the defect distribution maps generated as a result of inspection using a recipe after the present invention is applied. FIG. 19A and FIG. 20A show the defect maps immediately after inspection, FIG. 19B shows the defect map generated when defects are randomly sampled, and FIG. 20B shows the defect map generated when defects are sampled using the method according to the present invention. Note that FIG. 19A and FIG. 20A show the same number of defects and that FIG. 19B and FIG. 20B show the same number of defects.

As shown in the figures, only many concentrated defects in a particular area are sampled in the defect distribution map before the present invention is applied, shown in FIG. 19B, and, therefore, the defects cannot be confirmed or defect images cannot be obtained efficiently. As a result, the major defects in the process fail to be detected in many cases, the detected defects cannot fed back efficiently to the process, and the inspection efficiency is significantly decreased.

In contrast, the defect distribution map generated after the present invention is applied, shown in FIG. 20B, shows the result of defect inspection where a filter is executed to invalidate the minor defects in the wafer fabrication process, a cluster number is assigned to the concentrated defects, and, after that, a classification code is assigned according to the characteristics of the defects. An arbitrary number of defects with a classification code are sampled from the defects to which the cluster number is assigned, and an arbitrary number of defects with a classification code are sampled from the defects to which the cluster number is not assigned. As a result, the defect distribution map generated after the present invention is applied contains defects sampled evenly from the whole wafer, allowing the user to check defects and to obtain defect images more efficiently. This allows the user to detect all major defects in the process and to feed them back to the process efficiently.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A pattern inspection apparatus comprising:
substrate holding means for holding a substrate on which a pattern is formed;
application means for applying a laser beam, a beam, or a charged particle beam to the substrate held by said substrate holding means;
detection means for detecting a signal generated from the substrate by the application;
storage means for imaging and storing the signal detected by said detection means;
comparison means for comparing the image stored in said storage means with an another image formed from a pattern identical in design;
determination means for determining if defects are detected in the pattern based on the comparison result of said comparison means;
display means having a map display part where positions of defects on the substrate are displayed as a map, an image display part where defect images are displayed, a list display part where a list of defect information is displayed, and a graph display part where statistical information on selected defect items is displayed as a graph; and
area selection means for selecting an area included in the map displayed in said map display part,
wherein, when a map area is selected by said area selection means, a list of defect images of defects in the selected map area is displayed in said image display part and a list of defect information on defects in the selected map area is displayed in said list display part.

2. The pattern inspection apparatus according to claim 1, further comprising image selection means for selecting an image displayed in said image display part wherein, when an image is selected by said image selection means and a position of a defect in said map display part corresponding to the image are highlighted.

3. The pattern inspection apparatus according to claim 1, further comprising defect information selection means for selecting defect information displayed in said list display part wherein, when defect information is selected by said defect information selection means, a position of a defect in said map display part corresponding to the defect information and a defect image in said image display part corresponding to the defect information are highlighted.

4. The pattern inspection apparatus according to claim 1, further comprising a function for plotting a group of defects, to which a predetermined classification code is assigned, in a coordinate system whose axes indicate a plurality of items representing characteristics of the defects, for displaying a boundary line for including plotted points according to a predetermined ratio, and for registering an area surrounded by the boundary line into a recipe as a condition for assigning the classification code.

5. The pattern inspection apparatus according to claim 4, further comprising means for changing the boundary line via dragging.

6. The pattern inspection apparatus according to claim 1 wherein, when a radius and a number of elements are entered as a clustering condition and when there are continuous defects, each of which has defects no fewer than the number of elements within the radius, within a distance of the radius from a defect that is a center, a cluster number is assigned to each of the defects.

7. The pattern inspection apparatus according to claim 4, further comprising a function for confirming defects displayed in said image display part after executing a review condition registered in the recipe.

8. The pattern inspection apparatus according to claim 4, further comprising a function for saving defect images displayed in said image display part after executing a review condition registered in the recipe.

9. A pattern inspection apparatus comprising:
substrate holding means for holding a substrate on which a pattern is formed;
application means for applying a laser beam, a beam, or a charged particle beam to the substrate held by said substrate holding means;
detection means for detecting a signal generated from the substrate by the application;
storage means for imaging and storing the signal detected by said detection means;
comparison means for comparing the image stored in said storage means with an another image formed from a pattern identical in design;
determination means for determining if defects are detected in the pattern based on the comparison result of said comparison means;
display means having a map display part where positions of defects on the substrate are displayed as a map, an image display part where defect images are displayed, a list display part where a list of defect information is displayed, and a graph display part where statistical information on selected defect items is displayed as a graph; and
area selection means for selecting an area included in the map displayed in said map display part,
wherein a selected map area is displayed in said graph display part.

10. The pattern inspection apparatus according to claim 9, further comprising image selection means for selecting an image displayed in said image display part wherein, when an image is selected by said image selection means, a position of a defect in said map display part corresponding to the image and a display part in said graph display part to which a defect corresponding to the image belongs is highlighted.

11. The pattern inspection apparatus according to claim 9, further comprising graph selection means for selecting a display part in said graph display part wherein, when a part of the graph is selected by said graph selection means, a position of a defect in said map display part corresponding to a defect belonging to the selected part of the graph, a defect image in said image display part corresponding to a defect included in the selected part of the graph, and a defect included in the selected part of the graph are highlighted.

12. The pattern inspection apparatus according to claim 9, further comprising a function for plotting a group of defects, to which a predetermined classification code is assigned, in a coordinate system whose axes indicate a plurality of items representing characteristics of the defects, for displaying a boundary line for including plotted points according to a predetermined ratio, and for registering an area surrounded by the boundary line into a recipe as a condition for assigning the classification code.

13. The pattern inspection apparatus according to claim 12, further comprising means for changing the boundary line via dragging.

14. The pattern inspection apparatus according to claim 9 wherein, when a radius and a number of elements are entered as a clustering condition and when there are continuous defects, each of which has defects no fewer than the number of elements within the radius, within a distance of the radius from a defect that is a center, a cluster number is assigned to each of the defects.

15. The pattern inspection apparatus according to claim 9, further comprising means for setting au upper limit value and/or a lower limit value for the graph displayed in said graph display part and a function for registering the upper limit value and/or the lower limit value in a recipe as a filtering condition.

16. The pattern inspection apparatus according to claim 12, further comprising a function for confirming defects displayed in said image display part after executing a review condition registered in the recipe.

17. The pattern inspection apparatus according to claim 12, further comprising a function for saving defect images displayed in said image display part after executing a review condition registered in the recipe.

* * * * *